US008609824B2

(12) United States Patent
Ushijima

(10) Patent No.: US 8,609,824 B2
(45) Date of Patent: Dec. 17, 2013

(54) METHODS OF TREATMENT USING THYMUS-DERIVED COMPOSITIONS

(75) Inventor: Richard N. Ushijima, Wahaiwa, HI (US)

(73) Assignee: CMI Research Management, LLC, Wahaiwa, HI (US)

( * ) Notice: Subject to any disclaimer, the term of this patent is extended or adjusted under 35 U.S.C. 154(b) by 367 days.

(21) Appl. No.: 12/829,829

(22) Filed: Jul. 2, 2010

(65) Prior Publication Data

US 2011/0020464 A1 Jan. 27, 2011

Related U.S. Application Data

(60) Provisional application No. 61/230,529, filed on Jul. 31, 2009, provisional application No. 61/222,636, filed on Jul. 31, 2009, provisional application No. 61/228,709, filed on Jul. 27, 2009.

(51) Int. Cl.
*C07K 1/00* (2006.01)

(52) U.S. Cl.
USPC .......................................... 530/412

(58) Field of Classification Search
None
See application file for complete search history.

(56) References Cited

U.S. PATENT DOCUMENTS

| 4,010,148 | A | * | 3/1977 | Goldstein | ...................... | 530/399 |
| 4,077,949 | A | * | 3/1978 | Goldstein | ...................... | 530/301 |
| 4,826,680 | A | | 5/1989 | Jaeger | | |
| 5,976,537 | A | | 11/1999 | Mengeling | | |
| 2011/0020465 | A1 | | 1/2011 | Ushijima | | |

FOREIGN PATENT DOCUMENTS

WO    WO 2011/016937    2/2011

OTHER PUBLICATIONS

Ng et al., "Protective Effect of Houttuynia cordata Extract on Bleomycin-Induced Pulmonary Fibrosis in Rats", The American Journal of Chinese Medicine, vol. 35, No. 3, 465-475.*
Wingfield, P., Protein Precipitation Using Ammonium Sulfate, Curr. Protocols in Protein Sci., May 2001, Supplement 13, Appendix 3F: A.3F1-A.3F.8.*
Ng et al., "Protective Effect of Houttuynia cordata Extract on Bleomycin-Induced Pulmonary Fibrosis in Rats", The American Journal of Chinese Medicine, 2007, vol. 35, No. 3, 465-475.*
Akita et al., "New Assay Method for Surveying Anti-Emetic Compounds from Natural Sources," Natural Product Sciences, 1998, pp. 72-77, vol. 4.
Goldstein et al., "Thymosin and Other Thymic Hormones: Their Nature and Roles in Thymic Dependency of Immunological Phenomena," *Contemporary Topics in Immunobiology*, vol. 2 (Thymus Dependency), Davis/Carter (editors), 1973, Plenum Press, New York, p. 339-350.
Hayashi et al., "Virucidal Effects of the Steam Distillate from *Houttuynia cordata* and its Components on HSV-1, Influenza Virus, and HIV," Planta Med., 1995, pp. 237-241, vol. 61.
Hooper et al., "Purification and Properties of Bovine Thymosin," Annals of the New York Academy of Sciences, 1975, p. 125-144, vol. 249.
Hu et al., "Treatment of Bovine Mastitis with *Houttuynin* Sodium Bisulphate," Journal of Veterinary Medicine, 1977, pp. 365-370, vol. 44.
Huang, "Yu Xing Cao," *The Pharmacology of Chinese Herbs*, Second Edition, CRC Press, 1999, pp. 392-393.
Kawai et al., "Anti-Emetic Principles of *Magnolia obovata* Bark and *Zingiber officinale* Rhizome," Planta Med., 1994, pp. 17-20, vol. 60.
Khan et al., "Preliminary Screening of Methanol and Butanol Extracts of *Tamarindus indica* for Anti-Emetic Activity," Journal of Basic and Applied Sciences, 2005, pp. 51-54, vol. 1.
Kinoshita et al., "Anti-emetic principles of Inula linariaefolia flowers and *Forsythia suspensa* fruits," Phytomedicine, 1996, pp. 51-58, vol. 3.
Ohno et al., "Antitumor 1,3-β-Glucan from Cultured Fruit Body of *Sparassis crispa*," Biol. Pharm. Bull., 2000, pp. 866-872, vol. 23.
Tai et al., "Anti-Emetic Principles of *Poria cocos*," Planta Med., 1995, pp. 527-530, vol. 61.
U.S. Appl. No. 61/222,636, filed Jul. 31, 2009, entitled "Methods of Treatment of Gout Using Thymus-Derived Compositions," first inventor Ushijima.
U.S. Appl. No. 61/228,709, filed Jul. 27, 2009, entitled "Methods for Treatment of Cancer Using Thymus-Derived Compositions," first inventor Ushijima.
U.S. Appl. No. 61/230,529, filed Jul. 31, 2009; entitled "Methods of Treatment Using Thymus-Derived Compounds," first inventor Ushijima.
Yang et al., "Anti-emetic principles of *Pogostemon cablin* (Blanco) Benth," Phytomedicine, 1999, pp. 89-93, vol. 6.

* cited by examiner

*Primary Examiner* — Suzanne M Noakes
(74) *Attorney, Agent, or Firm* — Barry L. Davison; Davis Wright Tremaine LLP

(57) ABSTRACT

Embodiments of the present invention provide processes for preparing thymus extracts and plant or fungal extracts, and more particularly provide compositions (Thyex-1-6A and -6B) produced in accordance with said processes, and methods for treatment of various conditions comprising administration of said compositions including but not limited to impaired physical vigor or aptitude, and aging and/or age-related conditions (arthritis, mobility deficits, loss of appetite, etc.). Additional aspects provide methods for building muscle mass, for reducing exercise recovery period, or for sustaining exercise intensity. Particular aspects relate to preparation of *Houttuynia cordata* extracts and the use of those extracts as an anti-emetic and/or anti-nausea treatment for a subject in need thereof.

22 Claims, 5 Drawing Sheets

_US 8,609,824 B2_

METHODS OF TREATMENT USING THYMUS-DERIVED COMPOSITIONS

CROSS-REFERENCE TO RELATED APPLICATIONS

This application claims the benefit of priority to U.S. Provisional Patent Application Ser. Nos. 61/230,529, filed 31 Jul. 2009, entitled "Methods of Treatment Using Thymus-Derived Compositions"; 61/222,636, filed 31 Jul. 2009; entitled "Methods of Treatment of Gout Using Thymus-Derived Compositions"; and 61/228,709, filed 27 Jul. 2009, entitled "Methods for Treatment of Cancer Using Thymus-Derived Compositions". In addition, this application is related to the following copending patent applications: U.S. patent application Ser. No. 12/830,181, and International Application number PCT/US2010/040993, which are incorporated herein by reference in their entirety.

TECHNICAL FIELD OF THE INVENTION

Aspects of the present invention relate to processes for preparing thymus extracts and plant or fungal extracts, and more particularly provide compositions (Thyex-1-Thyex 6A and Thyex-6B) produced in accordance with said processes, and methods comprising administration of said compositions for stimulating or modulating the immune system, for building muscle mass, and for treatment of various conditions including but not limited to impaired immune status, impaired physical vigor or aptitude, and aging and/or age-related conditions (arthritis, mobility deficits, loss of appetite, etc.). Combination or adjunctive therapies (e.g, with antibiotics, etc.) are also encompassed. Particular aspects relate to preparation of _Houttuynia cordata_ extracts and novel uses of same for treating nausea (e.g., anti-nausea and/or anti-emetic).

BACKGROUND

Impaired physical vigor or aptitude. Loss of physical vigor has been associated with aging. In certain instances, aging athletes injected with growth hormone have reported "restoration" of physical vigor. Thymic hormone has been reported to affect the endocrine system; for example, to affect release by the pituitary of FSH and LH in thymectomized mice resulting in production of testosterone/estrogen.

Aging. All mammals possess a thymus gland at birth. As an animal ages, the gland begins to become fibrous and progressively degenerates. In humans, the thymus gland continues to grow until about age 20 before degenerating, and by age 50, no trace of glandular tissue is present. The progressive loss of the thymus can be temporally correlated to with diminishing natural physical stamina, and increasing incidence of age-related disorders.

There is a pronounced need in the art for economically-viable treatments for immune modulation or stimulation, and the effective treatment and prevention of impaired physical vigor and stamina, and age-related disorders, including age-related loss of natural physical stamina.

SUMMARY OF THE INVENTION

Particular embodiments of the present invention provide inventive methods for preparing thymus extracts (Thyex-1-6A and -6B; see working EXAMPLES 1-8), and therapeutic compositions comprising said Thyex preparations.

Additional exemplary embodiments provide methods for treating at least one condition selected from the group consisting of aging and related conditions, restoration of athletic vigor and/or stamina (EXAMPLE 9), allergy and autoimmune disorders (e.g., lichen sclerosis set atrophicus, rheumatoid arthritis, psoriasis, progressive systematic scleroderma, lupus, and juvenile diabetes) (EXAMPLE 11), post-surgical treatment and/or wound healing (EXAMPLE 12), emphysema, and inflammation (EXAMPLE 13), comprising administration of a Thyex composition as described herein.

In preferred embodiments, the Thyex compositions are use to stimulate or modulate the immune system, or to treat impaired physical vigor or aptitude, and aging and/or age-related conditions (arthritis, mobility deficits, loss of appetite, etc.).

Specifically, particular embodiments of the present invention provide methods for preparing thymus extract compositions (Thyex-1-6A and -6B; EXAMPLES 1-8) for the treatment of impaired physical vigor and stamina, and age-related disorders, comprising: homogenizing thymus tissue; removing tissue debris therefrom to produce a supernatant; and concentrating and denaturing the supernatant to produce a clarified supernatant fraction. Preferably, the processes comprise further clarifying of the clarified supernatant by high-speed centrifugation at about 8,500 (g). Preferably the processes further comprise filter sterilizing. Preferably, the pH and ionic strength of the resulting supernatant are physiologically compatible. Preferably, the pH and ionic strength of the resulting supernatant have values of about 7 and of about 0.85% (w/v), respectively. Preferably, the initial ratio of thymus tissue to aqueous homogenization fluid is about 350 g wet weight of thymus tissue to about 0.7 L of homogenization fluid. Preferably, the processes comprise further fractionating based on molecular weight to obtain a final fraction having proteins of about 3.5 to about 30 kDa.

Additional embodiments provide processes for preparing thymus extract compositions for the treatment of impaired physical vigor and stamina, and age-related disorders, comprising: homogenizing thymus tissue; removing tissue debris therefrom to produce a supernatant; concentrating, denaturing, and clarifying the supernatant fraction; further concentrating the clarified supernatant fraction to produce a further concentrated fraction; fractionating the further concentrated fraction to remove molecules having a molecular weight less than about 3.5 kDa; and further fractionating based on molecular weight to obtain a final fraction having proteins of about 3.5 to about 30 kDa. Preferably, the processes further comprise adjusting the pH and/or ionic strength, of the final fraction to a physiological or therapeutically compatible value. Preferably, said adjusting is achieved by adding phosphate buffer and/or sodium chloride to produce a solution having a pH value of about 7, and/or an ionic strength of about 0.85% (w/v). Preferably the processes further comprise filter sterilizing. Preferably, said sterilizing is achieved by using a 0.2µ membrane filter. Preferably, the initial ratio of thymus tissue to aqueous homogenization fluid is about 350 g wet weight (about 400 ml) of thymus tissue to about 0.7 L of homogenization fluid.

Further embodiments provide compositions for body building supplements, including protein supplements for use in building muscle mass, comprising: thymus extract compositions (Thyex-1-6A and -6B) produced in accordance with the above-described processes, and a pharmaceutically acceptable carrier.

Yet further embodiments provide pharmaceutical compositions for the treatment of impaired physical vigor and stamina, and age-related disorders, comprising: thymus extract compositions (Thyex-1-6A and -6B) produced in accordance with the above-described processes, and a pharmaceutically acceptable carrier.

Further embodiments provide compositions for body building supplements, including protein supplements for use in building and/or increasing muscle mass and/or as part of an exercise supplement composition comprising: thymus extract compositions (Thyex-1-6A and -6B) produced in accordance with the above-described processes.

Still further embodiments provide methods for treating impaired physical vigor and stamina, and age-related disorders, comprising: administering of a therapeutically-effective amount to a mammal in need thereof a thymus extract composition (Thyex-1-6A and -6B) produced in accordance with the above-described processes, and wherein the mammal, includes, but is not limited to human, canine, feline, bovine, equine (e.g., race horse), ovine, and porcine. Even further embodiments provide for methods of treating an age-related condition wherein the age-related condition is at least one selected from the group consisting of arthritis, mobility deficits, muscle mass loss, impaired vigor, and loss of appetite. Even further embodiments provide for methods of treating an impaired physical vigor, stamina or aptitude, wherein the impaired physical vigor stamina or aptitude is selected from the group consisting of decreased stamina, and impaired recovery from exercise or physical stress. Preferably, the thymus extract composition is administered in combination with administration of macrophage stimulating agent.

According to certain aspects, the inventive Thyex compositions are useful in reducing exercise recovery period and/or for sustaining exercise intensity, comprising: administering of a therapeutically-effective amount of a thymus extract composition (Thyex-1-6A and -6B) produced in accordance with the herein-described processes.

According to additional aspects, the inventive Thyex compositions are useful for immuno stimulation and/or immunoregulation, comprising administering to a mammalian subject in need thereof a therapeutically-effective amount of a thymus extract composition (Thyex-1-6A and -6B) produced in accordance with the herein-described processes. According to further aspects, the inventive Thyex compositions are useful for modulating endocrine function, comprising administering to a mammalian subject in need thereof a therapeutically-effective amount of a thymus extract composition (Thyex-1-6A and -6B) produced in accordance with the herein-described processes.

According to still further aspects, the inventive Thyex compositions are useful for treating or preventing, virus infection, virus-associated conditions or secondary infection, or wasting syndrome in an affected or susceptible swine in need thereof, comprising administering to the swine a therapeutically-effective amount of a thymus extract composition (Thyex-1-6A and -6B) produced in accordance with the herein-described processes.

According to certain aspects, the inventive Thyex compositions are used in combination with administering an antimicrobial agent (e.g. an antibiotic or a *Houttuynia cordata* extract composition).

According to further aspects, the inventive Thyex compositions are useful for treating nausea, comprising administration to a mammalian subject in need thereof a therapeutically-effective amount of an extract of *Houttuynia cordata*.

According to additional aspects (see working EXAMPLES 14-16), the inventive Thyex compositions are used in the treatment of a disease or condition caused by or related to the Arteriviridae family of viruses (like PRRS), PRRS-related conditions and secondary infections (e.g., diarrhea, pneumonitis and/or intestinal disorders), and wasting syndrome in pregnant gilts and sows, and in swine being fattened for slaughter. According to particular aspects, adjunct treatment of swine with Thyex compositions is effective to enhance the efficacy of vaccine regimens in protecting PRRSV-susceptible reproductive systems against virulent field strains of PRRSV. According to further aspects, strains of PRRSV can be selected from the group consisting of strains of PRRSV of either European or North American serotype, VR-2332 and Lelystad virus strains, NADC-8, NADC-9, and NVSL-14 strains, modified PRRSV strains, attenuated PRRSV strains, and combinations thereof. According to yet further aspects, the vaccine element is a monovalent, bivalent or polyvalent PRRSV-based vaccine, or an immunogenic or antigenic component of a PRRSV strain, or a modified or attenuated form of a PRRSV strain or PRRSV immunogen.

Particular embodiments of the present invention provide inventive methods for preparing palatable *Houttuynia cordata* extract composition having anti-nausea and/or anti-emetic activity, comprising: performing an aqueous extraction of *Houttuynia cordata* plant material to produce a aqueous extract and an extracted plant material; separating the aqueous extract from the extracted plant material to provide a separated aqueous extract; and heat distilling a volume of the separated aqueous extract and collecting a fractional volume of initial distillate to provide a substantially non-bitter, heat-distilled *Houttuynia cordata* extract composition having anti-nausea and/or anti-emetic activity. Further particular embodiments of the present invention provide methods for preparing palatable *Houttuynia cordata* extract composition, wherein at least one of the *Houttuynia cordata* plant material, aqueous extract and the separated aqueous extract is frozen.

Yet further particular embodiments of the present invention provide methods for preparing palatable *Houttuynia cordata* extract composition, wherein the aqueous extraction comprises aqueous extraction with heated or boiling water. Still further particular embodiments of the present invention provide methods for preparing palatable *Houttuynia cordata* extract composition, wherein separating comprises filtering and/or centrifugation.

According to certain aspects, the present invention provides methods for preparing palatable *Houttuynia cordata* extract composition, wherein separating comprises centrifugation, optimally at 3,500×G for 10 minutes at ambient temperature to produce a pellet, and an aqueous supernatant fraction. According to further aspects, the present invention provides methods for preparing palatable *Houttuynia cordata* extract composition, wherein separating comprises centrifugation to provide an aqueous supernatant fraction, and filtration of the aqueous supernatant fraction. According to yet further aspects, the present invention provides methods for preparing palatable *Houttuynia cordata* extract composition, wherein distilling comprises distilling at a temperature of about 100° C. or greater, and wherein distillation is allowed to proceed until the volume of distillate is about half of the initial primary aqueous extract. According to still further aspects, the present invention provides methods for preparing palatable *Houttuynia cordata* extract composition, further comprising adjusting of at least one of pH and ionic strength to provide at least one of a pH-adjusted and ionic strength-adjusted distillate fraction. According to still further aspects, the present invention provides methods for preparing palatable *Houttuynia cordata* extract composition, further comprising sterilizing of the distillate.

Particular embodiments of the present invention provide for compositions or extracts of *Houttuynia cordata* plant material prepared according to the disclosed inventive methods. Further embodiments of the present invention provide for methods of treating nausea, comprising administration to a subject in need thereof a therapeutically effective amount of a heat-distilled aqueous extract of *Houttuynia cordata* plant material, or of derivative thereof having anti-nausea activity. Still further embodiments of the present invention provide for methods of screening or identifying a composition for treating nausea, comprising: preparing a heat-distilled aqueous extract of *Houttuynia cordata* plant material; fractionating components of the extract; and assaying at least one fraction for anti-nausea or anti-emetic activity, or an indicator thereof.

DETAILED DESCRIPTION OF THE INVENTION

Figure 1:
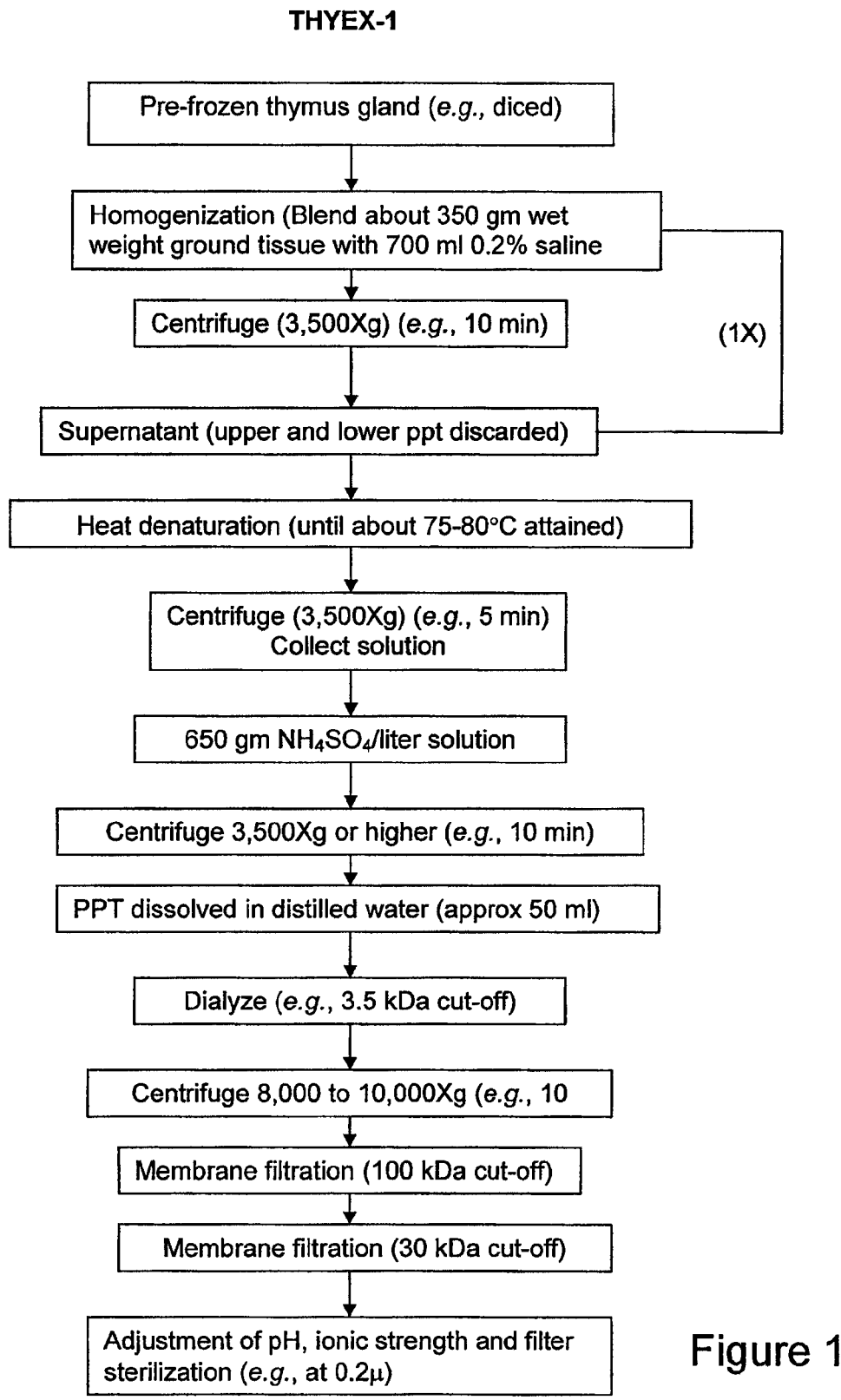
FIG. 1 is a flow diagrammatic representation comprising an inventive Thyex-1 process embodiment for preparing a thymus extract composition.
Figure 2:
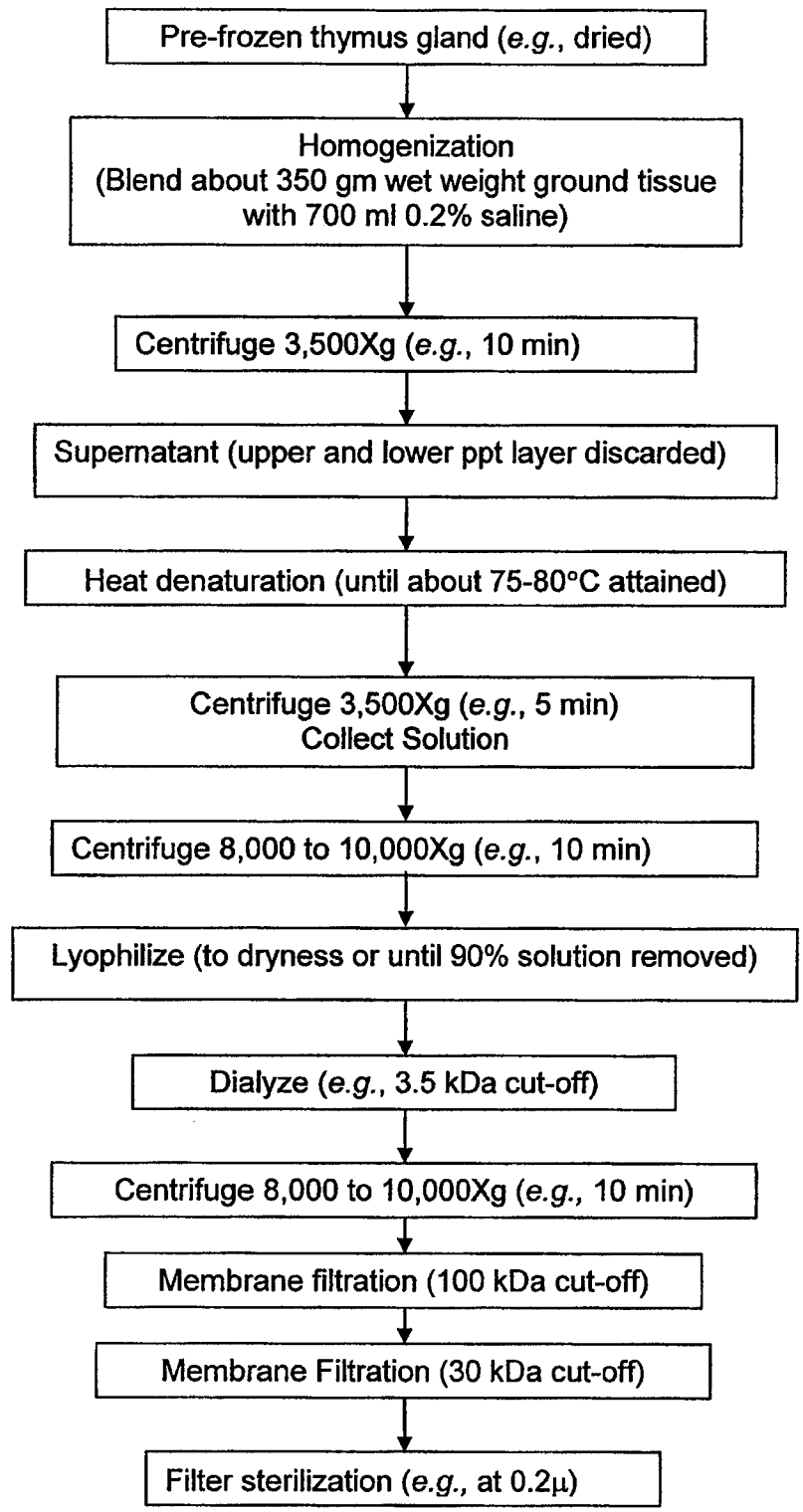
FIG. 2 is a flow diagrammatic representation comprising an inventive Thyex-2 process embodiment for preparing a thymus extract composition.
Figure 3:
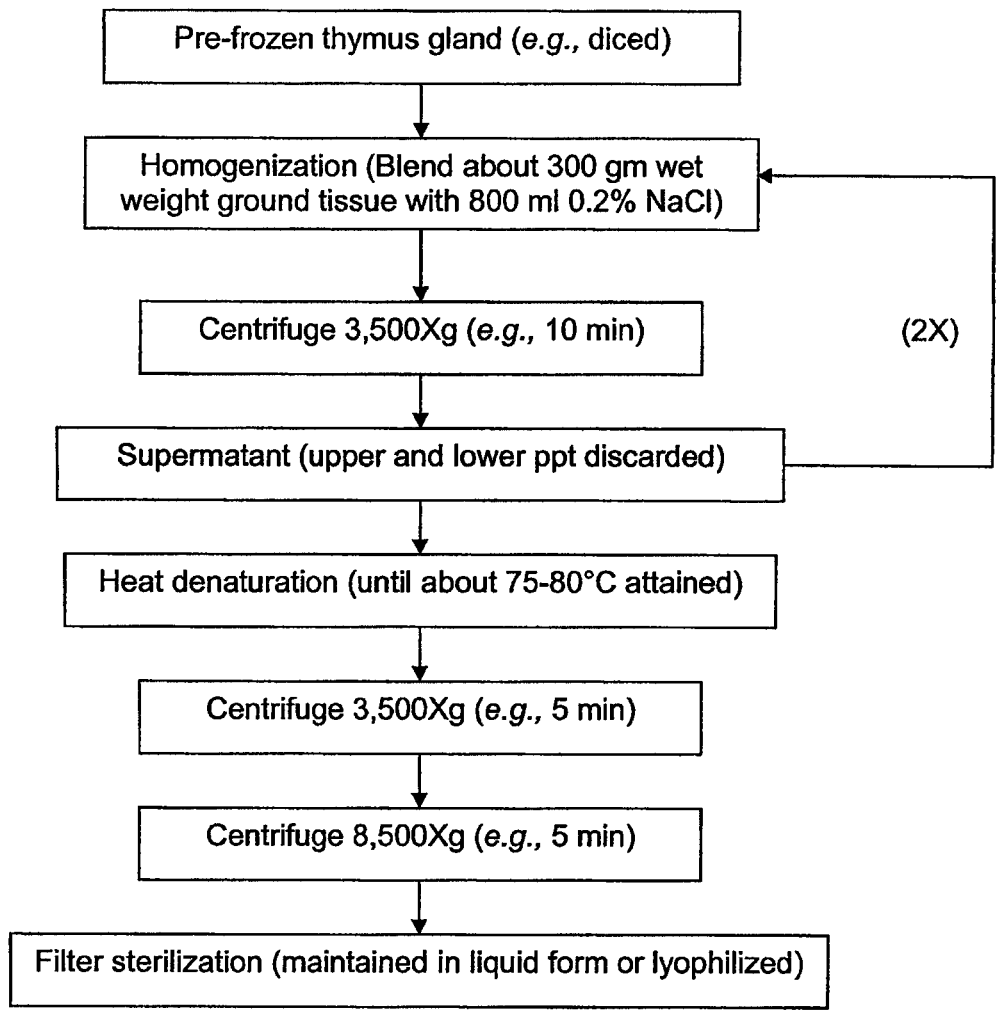
FIG. 3 is a flow diagrammatic representation comprising an inventive Thyex-3 process embodiment for preparing a thymus extract composition.

Aspects of the present invention relate to processes for preparing thymus extracts and plant or fungal extracts, and more particularly provide compositions (Thyex-1-6A and -6B) produced in accordance with said processes, and administration of said compositions in methods for treatment of at least one condition selected from the group consisting of aging and related conditions, restoration of athletic vigor and/or stamina, allergy and autoimmune disorders (e.g., lichen sclerosis set atrophicus, rheumatoid arthritis, psoriasis, progressive systematic scleroderma, lupus, and juvenile diabetes), emphysema, and inflammation.

In particular aspects, administration of said compositions is used for treatment of impaired physical vigor or aptitude, and aging and/or age-related conditions (arthritis, mobility deficits, loss of appetite, etc.).

In preferred aspects, the inventive compositions (Thyex-1-6A and -6B) are administered in combination with a macrophage stimulating agent.

Particular aspects provide a method for preparing heat-treated, fractionated thymus extract composition, comprising: homogenizing thymus tissue with aqueous homogenization fluid to produce an aqueous thymus homogenate; removing tissue debris from the aqueous thymus homogenate to produce a primary supernatant; heat denaturing the primary supernatant, and clarifying the denatured primary supernatant by use of at least one of low-speed centrifugation and filtration, to produce a clarified supernatant; and separating molecules having molecular weights less than about 3.5 kDa from the clarified supernatant, wherein a heat-treated, fractionated thymus extract composition lacking proteins or polypeptides having molecular weights less than about 3.5 kDa is provided. In certain aspects, the method further comprises separating molecules having molecular weights greater than about 30 kDa from the heat-treated, fractionated thymus extract composition, wherein a heat-treated, fractionated thymus extract composition comprising proteins or polypeptides having molecular weights in the range of about 3.5 kDa to about 30 kDa is provided. In certain embodiments, the method comprises further clarifying of the clarified supernatant by high-speed centrifugation to produce a final clarified supernatant fraction, and optionally sterilizing the final clarified supernatant fraction to produce a sterile final clarified supernatant fraction. In certain aspects, sterilizing is achieved by passing the final clarified supernatant fraction through a membrane filter. In particular embodiments, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. In certain aspects, heat denaturing and clarifying of the primary supernatant is achieved by heat denaturation, followed by low-speed centrifugation and crude filtration to remove particulate matter. In certain embodiments, the methods further comprise lyophilization of the final clarified supernatant fraction. Preferably no steps involving exogenously added protease digestion, or extraction with organic solvents are used.

Additional particular aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; heat denaturing the primary supernatant, and clarifying the denatured primary supernatant by use of at least one of low-speed centrifugation and filtration to produce an intermediate clarified supernatant; concentrating the intermediate clarified supernatant to produce a concentrated intermediate fraction; and separating molecules having molecular weights less than about 3.5 kDa from the concentrated intermediate fraction, wherein a heat-treated, fractionated thymus extract composition lacking proteins or polypeptides having molecular weights less than about 3.5 kDa is provided. In certain embodiments, the method further comprises separating molecules having molecular weights greater than about 30 kDa from the heat-treated, fractionated thymus extract composition, wherein a heat-treated, fractionated thymus extract composition comprising proteins or polypeptides having molecular weights in the range of about 3.5 kDa to about 30 kDa is provided. Certain embodiments further comprise clarifying of the concentrated intermediate fraction by high-speed centrifugation to produce a final clarified supernatant fraction. Particular aspects further comprise adjusting at least one of the pH or ionic strength of the fraction having proteins or polypeptides of molecular weight of about 3.5 to about 30 kDa to a physiological or therapeutically compatible value, to produce a pH- or ionic strength-adjusted fraction, and in certain aspects, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. Certain embodiments further comprise sterilizing the pH-, or ionic strength-adjusted fraction to produce a sterile pH-, or ionic strength-adjusted fraction, and in particular aspects, sterilizing is achieved by passing the fraction through a membrane filter. In particular embodiments, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. For particular embodiments, heat denaturing and clarifying of the primary supernatant is achieved by heat denaturation, followed by low-speed centrifugation and crude filtration to remove particulate matter. In particular embodiments, concentrating the intermediate supernatant involves concentrating and fractionating, wherein the concentrating and fractionating is achieved by adding ammonium sulfate to the intermediate clarified supernatant, followed by low-speed centrifugation and suspension of the resulting ammonium sulfate pellet in an aqueous solution to provide a concentrated intermediate fraction. In particular aspects, separating molecules having molecular weights less than about 3.5 kDa from the concentrated intermediate fraction comprises dialysis of the concentrated intermediate fraction, followed by high-speed centrifugation to remove particulate matter, to provide for a clarified concentrated intermediate fraction lacking proteins or polypeptides having molecular weights less than about 3.5 kDa. In certain embodiments, separating molecules having molecular weights greater than about 30 kDa from the heat-treated, fractionated thymus extract composition, is achieved by passing the clarified concentrated intermediate fraction lacking proteins or polypeptides having molecular weights less than about 3.5 kDa consecutively through a first and a second membrane filter having exclusion limits of about 100 and about 30 kDa, respectively, and collecting the filtrate. Particular aspects further comprise lyophilization of the heat-treated, fractionated thymus extract composition comprising proteins or polypeptides having molecular weights in the range of about 3.5 kDa to about 30 kDa.

Yet additional particular aspects provide a composition or pharmaceutical composition, comprising a thymus extract composition produced in accordance with the methods recited herein.

Additional aspects provide a body building supplement, comprising a thymus extract composition produced in accordance with the methods recited herein. In certain embodiments, the supplement comprises a protein supplement for use in building muscle mass.

Particular embodiments further comprise administering a macrophage stimulating agent in combination with administration of the thymus extract composition for use in treating at least one condition selected from the group consisting of aging and related conditions, restoration of athletic vigor and/or stamina, allergy and autoimmune disorders (e.g., lichen sclerosis set atrophicus, rheumatoid arthritis, psoriasis, progressive systematic scleroderma, lupus, and juvenile diabetes), emphysema, and inflammation. In certain aspects, the macrophage stimulating agent comprises at least one of beta glucan, polysaccharides, toxoid vaccines, and Staph lysate vaccine, immune complexes, compliment components, lymphokinesm, tuftsin, lipopolysaccharides (LPS), muramyl dipeptide, physiologic cation complexing agents, pyran copolymers, polycarboxylates, ionphores, Quadrol (N,N,N', N'-tetrakis(2-hydroxypropyl)ethylenediamine), and macrophage stimulating peptides. In certain aspects, the beta glucan comprises beta 1,3 glucan.

Additional aspects provide a method for treating aging or an age-related symptom or condition, comprising administering to a mammalian subject in need thereof a therapeutically-effective amount of a thymus extract composition produced in accordance with the methods recited herein, wherein at least one age-related symptom or condition is treated or alleviated. In certain aspects the mammal is a human. In particular aspects, the age-related condition is at least one selected from the group consisting of arthritis, mobility deficits, muscle mass loss, impaired vigor, and loss of appetite.

Additional aspects provide a method for reducing exercise recovery period or for sustaining exercise intensity, comprising administering to a mammalian subject in need thereof a therapeutically-effective amount of a thymus extract composition produced in accordance with the methods recited herein, wherein at least one of reducing exercise recovery period, and sustaining exercise intensity is afforded. In certain aspects, the thymus extract composition is administered with, or as part of an exercise supplement composition.

Yet additional aspects provide a method for treating impaired physical vigor or aptitude, comprising administering to a mammalian subject in need thereof a therapeutically-effective amount of a thymus extract composition produced in accordance with the methods recited herein, wherein at least one symptom or condition of impaired physical vigor or aptitude is treated or alleviated. In certain aspects, the at least one symptom or condition of impaired physical vigor or aptitude is at least one selected from the group consisting of decreased stamina, and impaired recovery from exercise or physical stress.

Additional aspects provide a method for increasing muscle mass, comprising administering to a mammalian subject in need thereof an effective amount of a thymus extract composition produced in accordance with the methods recited herein, wherein increasing muscle mass is afforded.

Certain aspects provide a method for treating arthritis and age-related issues, comprising administering to a mammalian subject in need thereof an effective amount of a thymus extract composition produced in accordance with the methods recited herein, wherein effects of arthritis and age-related issues is alleviated. According to particular aspects, the mammalian subject in need of treatment includes but is not limited to canine, feline, bovine, porcine, equine, ovine, and other large animals. According to further aspects, the method for treating arthritis and age-related issues includes veterinary applications. According to still further aspects, the veterinary applications include but are not limited to treating canine, feline, bovine, porcine, equine, ovine, and other large animals.

Further aspects provide a method for immuno stimulation or immunoregulation, comprising administering to a mammalian subject in need thereof a therapeutically-effective amount of a thymus extract composition produced in accordance with the methods recited herein, wherein at least one of immuno stimulation or immunoregulation is afforded.

Yet further aspects provide a method for endocrine modulation, comprising administering to a mammalian subject in need thereof a therapeutically-effective amount of a thymus extract composition produced in accordance with the methods recited herein, wherein endocrine modulation is afforded.

Additional aspects provide methods for treating or preventing PRRS, PRRS-associated conditions or secondary infection, and wasting syndrome in an affected or susceptible swine in need thereof, comprising administering to the swine a therapeutically-effective amount of a thymus extract composition produced in accordance with the methods recited herein.

Definitions

"Thymus extract" or thymus extract composition, refers to a composition produced in accordance with one or more of the Thyex-1, -2, -3, -4, -5, -6A and -6B processes disclosed herein.

"*Houttuynia cordata*" extract refers to a compositions produced in accordance with the on or more of the D-YXC-1 and 2 processes disclosed herein.

"Animals" as used herein for treatment of subjects refers to chicken, duck, fish, hamster, rat, guinea pig, human, canine, feline, bovine, equine (e.g., race horse), ovine, goat, and porcine.

"Anti-microbial agent" means an agent with, for example, antibacterial, antifungal or antiviral activity, including, but not limited to: plant extracts (e.g., *Houttuynia cordata* extracts); antibiotics, such as β-lactam antibiotics, erythromycin compounds, Tetracycline compounds, aminoglycoside antibiotics, cephalosporin compounds, anthracycline compounds, phleomycin group antibiotics, sulfonamide compounds, macrolide antibiotics (e.g., tylosin, desmycosin, macrocin, and lactenocin), quinolone and quinolonyl compounds (e.g., quinolonyl lactams and quinolone thioureas, and carbacephem- and carbapenem-quinolones) carbapenem compounds, along with those antibiotic agents more commonly used in the swine industry, such as lankacidin-group antibiotics and derivatives, diterpene antibiotics (e.g, tiamulin-type), polyether or polycyclic ether antibiotics and derivatives (e.g., A82810), lysocellin, treponemycin, antibiotic 10381b, antibiotics GE 37468 A, B and C, A41030 antibiotics, antibiotic A47934, antibiotic BN-109, apramycin, actaplanin antibiotics, antibiotic A3823, antibiotic X-14766A, dihydromocimycin antibiotics, BM123γ-type antibiotics, antibiotic AV290, antibiotic A-32887, glycopeptide antibiotic UK-68,597, valnemulin, tiamulin, oxytetracyclin, chlortetracycline, tylosin, and manganese-containing antibiotic agents, copper-containing bleomycin group antibiotics; antifungal agents, such as partanamicins, fusacandins; and antihelminthic agents such as spiroketals, avermectin and milbemycin; and combinations thereof.

"Crude filtration" or "coarse filtration" means filtering a solution having particulate, precipitated or flocculent suspended material through, e.g., one or more layers of standard cheese cloth, or other sieving device (e.g., screen, strainer, colander, etc.), to remove said material.

"Low-speed centrifugation" means centrifugation at about 3,500×g (±5% or ±10%) for about 5-10 minutes (±5% or ±10%), or an equivalent sedimentation protocol thereof.

"High-speed centrifugation" means centrifugation at about 8,500×g (±5% or ±10%) for about 10 minutes (±5% or ±10%), or the equivalent sedimentation protocol thereof.

"Clarifying," or clarification of a supernatant fraction means removing particulate matter (e.g., precipitates, bacteria) from a solution containing such particulate matter through the use of standard separation techniques, such as low- or high-speed centrifugation (as defined above) or filtration.

With respect to fractionation of the particular supernatant fractions, the phrase "less than about 3.5 kDa" as used herein refers to less than 3.5 kDa, or less than a molecular weight that varies by ±5% or ±10% therefrom. Similarly, the phrase "proteins or polypeptides of molecular weight of about 3.5 to about 30 kDa" as used herein refers to proteins or polypeptides in a molecular weight ranged from 3.5 kDa, or from a molecular weight that varies by ±5% or ±10% therefrom, to 30 kDa, or to a molecular weight that varies by ±5% or ±10% therefrom.

With respect to pH and ionic strength, the phrase "a pH value of about 7, or an ionic strength of about 0.85% w/v." as used herein refers to a pH of 7 or a pH that varies by ±5% or ±10% therefrom, and/or an ionic strength of 0.85% w/v, or an ionic strength that varies by ±5% or ±10% therefrom.

"Vaccine" is defined herein in its broad sense to refer to any type of biological agent, administrable for the purpose of priming, enabling or enhancing an immune response against in an animal inoculated with the vaccine.

"Unpalatable," as used herein, refers to the art-recognized off-putting and/or bitter flavor widely recognized in the context of *Houttuynia cordata* extract. For example, those familiar with *Houttuynia cordata* extract (e.g., tea) described it as being bitter and/or fishy and that this flavor renders the extract largely unpalatable. The disclosed invention not only provides for separation of the unpalatable and palatable portions but also allows for separation of the anti-nausea and/or anti-emetic activity from the largely unpalatable portion using the heat-distilled technique as herein disclosed. The term "separation," as used herein can mean either separation of the unpalatable taste from the palatable taste in particular embodiments, or in alternate embodiments can mean loss of the unpalatable taste. "Unpalatable", as used herein, refers in particular embodiments to the non-heat-distilled *Houttuynia cordata* extract (e.g., the aqueous extract and the separated aqueous extract) being unpleasant, inedible, indigestible, disgusting, revolting, foul-tasting, nasty, bad, distasteful, disagreeable, bitter, offensive, unattractive, horrid, unsavory, displeasing, and repugnant.

"Bitter" and "bitterness," as used herein, refers in particular embodiments to the flavor the non-heat-distilled *Houttuynia cordata* extract (e.g., the aqueous extract and the separated aqueous extract). In particular, bitter refers to being or inducing the one of the four basic taste sensations that is particularly acrid, astringent, or disagreeable and suggestive of an infusion of hops.

"Substantially non-bitter," as used herein, refers in particular embodiments to reducing the bitterness/foulness of the extract by approximately half of the original non-heat-distilled *Houttuynia cordata* extract (e.g., the aqueous extract and the separated aqueous extract) or by reducing the bitterness/foulness to such a level that one would reasonably regard the solution as being palatable and/or without a unpleasant, inedible, indigestible, disgusting, revolting, foul-tasting, nasty, bad, distasteful, disagreeable, bitter, offensive, unattractive, horrid, unsavory, displeasing, and repugnant flavor. "Substantially non-bitter," as used herein, refers in particular embodiments to reducing the bitterness/foulness of the extract by approximately 60%. Preferably, particular embodiments relate to reducing the bitterness/foulness of the extract by approximately 70%. More preferably, particular embodiments relate to reducing the bitterness/foulness of the extract by approximately 75%. Even more preferably, particular embodiments relate to reducing the bitterness/foulness of the extract by approximately 80%. Still more preferably, particular embodiments relate to reducing the bitterness/foulness of the extract by approximately 85%. Most preferably, particular embodiments relate to reducing the bitterness/foulness of the extract by approximately 90%.

Methods for Preparing Thymus Extracts:

Particular embodiments of the present invention (see working EXAMPLES 1-8) provide novel processes for preparing therapeutically useful extracts (Thyex-1-6A and -6B) of thymus tissue. In particular aspects, the inventive processes are readily distinguishable from other known processes for preparing thymus extracts (e.g., Goldstein & White, Contemp. Topics in Immunobiology, p 339, 1973; Bergesi et al., *Folio Allergol. Immunol. Clin.* 21:201, 1977; Hooper et al., "The purification and properties of bovine thymosin," *Ann. NY Acad. Sci.* 249:125, 1975; U.S. Pat. No. 4,826,680, issued 2 May 1989 to Jaeger, Pharmaceutical Composition Containing Thymus Extract Fractions), and lack steps involving decalcite ($CaCO_3$) treatment, protease digestion, extraction with organic solvents (e.g., phenol, acetone or ethanol) or fractionation by column chromatography. Not only are the inventive compositions surprisingly effective in view of the teachings of the art, but the compositions produced in accordance with the instant processes are also further distinguished from those of the prior art by the molecular weight ranges of their protein elements.

The instant processes comprise steps to optimize protein compositions for therapeutic use of. For example, particular of the below-described process embodiments (Thyex-1-6A and -6B) are designed to provide therapeutic compositions, and include ammonium sulfate precipitation/fractionation and/or lyophilization steps, respectively, to facilitate optimal protein concentration and fractionation. The Thyex-3 process embodiment lacks an ammonium sulfate or lyophilization step, but provides for a sufficiently-concentrated composition by reusing (and thereby augmenting) an initial tissue homogenization supernatant fraction as homogenization fluid to homogenize additional tissue. The resulting Thyex-3 composition is less refined relative to those of Thyex-1 and Thyex-2, but is nonetheless suitably concentrated and formulated for efficacious delivery. The Thyex 6A and Thyex 6B process embodiments described below are designed to provide therapeutic compositions suitable for delivery as a topical ointment or by injection or inhalation, and include ammonium sulfate precipitation/fractionation steps. Thyex 5 is prepared from a similar process but is less refined (less fractionated) than Thyex 6A or Thyex 6B and is optimally mixed with an amount of an extracted lyophilized herbal source composition, and administered orally in filled gelatin capsules. The Thyex 4 process embodiment lacks ammonium sulfate precipitation step but comprises lyophilization to provide for a sufficiently-concentrated composition. The resulting Thyex 4 composition is less refined in relative to those of Thyex 5 or Thyex 6A or 6B, but is nonetheless suitably concentrated and formulated for efficacious oral deliver in both animals and humans.

Figure 4:
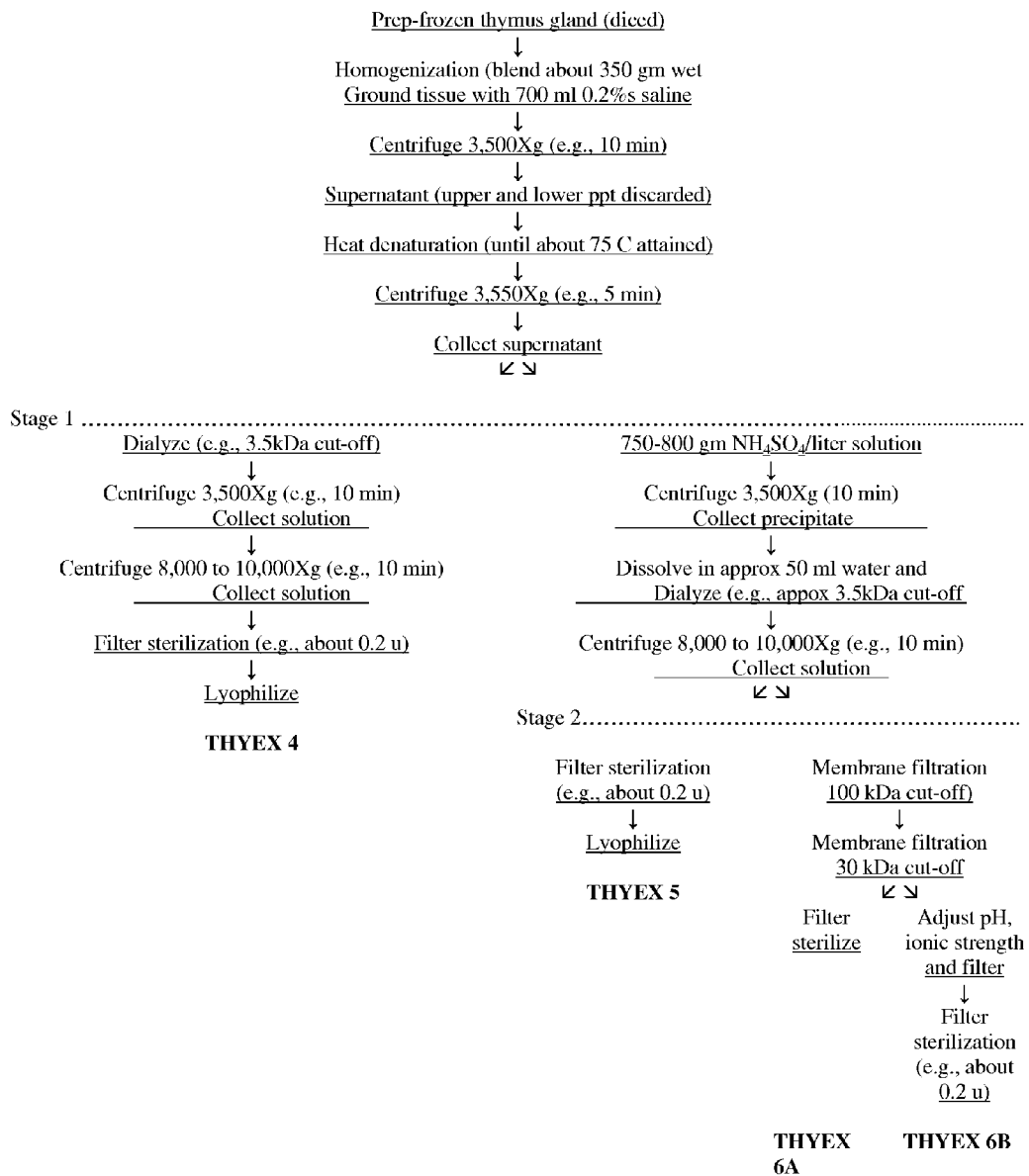
FIG. 4 is a flow diagrammatic representation comprising an inventive Thyex-4, -5 and -6 process embodiments for preparing a thymus extract composition.

Preferably, the thymus preparations are those comprising Thyex-4,5-, -6A and -6B (see FIG. 4, and EXAMPLES 4-8).

Particular specific aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; and heat denaturing and clarifying the primary supernatant to produce a clarified supernatant. In certain aspects, the method further comprises further clarifying of the clarified supernatant by high-speed centrifugation to produce a final clarified supernatant fraction. In certain embodiments, the method further comprises sterilizing the final clarified supernatant fraction to produce a sterile final clarified supernatant fraction. In particular aspects, sterilizing is achieved by passing the final clarified supernatant fraction through a membrane filter. In particular implementations, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. In particular aspects, heat denaturing and clarifying of the primary supernatant is achieved by heat denaturation, followed by low-speed centrifugation and crude filtration to remove particulate matter. In certain implementations, the method further comprises lyophilization of the final clarified supernatant fraction.

Additional aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; heat denaturing and clarifying the primary supernatant to produce an intermediate supernatant; and concentrating the intermediate supernatant to produce a concentrated intermediate fraction. In certain aspects, the method further comprises further clarifying of the concentrated intermediate fraction by high-speed centrifugation to produce a final clarified supernatant fraction. In particular embodiments, the method further comprises fractionating the final clarified supernatant fraction to remove molecules having a molecular weight less than about 3.5 kDa to produce a fractionated intermediate fraction. In certain aspects, the method further comprises fractionating the fractionated intermediate fraction, based on molecular weight, to obtain a fraction having proteins of about 3.5 to about 30 kDa. In particular implementations, the method further comprises adjusting at least one of the pH or ionic strength of the fraction having proteins of about 3.5 to about 30 kDa to a physiological or therapeutically compatible value, to produce a pH- or ionic strength-adjusted fraction. In certain aspects, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. In certain aspects, the method further comprises sterilizing the pH-, or ionic strength-adjusted fraction to produce a sterile pH-, or ionic strength-adjusted fraction. In particular embodiments, sterilizing is achieved by passing the fraction through a membrane filter. In certain aspects, the initial ratio of thymus tissue to aqueous homogenization fluid is about 350 g wet weight of thymus tissue to about 0.7 L of homogenization fluid. In particular embodiments, removing tissue debris from the aqueous thymus homogenate is achieved by a combination of low-speed centrifugation and crude filtration. In certain aspects, heat denaturing and clarifying of the secondary supernatant is achieved by heat denaturation, followed by low-speed centrifugation and crude filtration to remove particulate matter. In particular implementations, concentrating the intermediate supernatant involves concentrating and fractionating, and wherein the concentrating and fractionating is achieved by adding ammonium sulfate to the intermediate supernatant, followed by low-speed centrifugation and suspension of the resulting ammonium sulfate pellet in an aqueous solution. In some embodiments, fractionating the concentrated intermediate fraction to remove molecules having a molecular weight less than about 3.5 kDa is achieved by dialysis of the concentrated intermediate fraction, followed by high-speed centrifugation to remove particulate matter. In particular aspects, fractionating the fractionated intermediate fraction, based on molecular weight, is achieved by passing the fractionated intermediate fraction consecutively through a first and a second membrane filter having exclusion limits of about 100 and about 30 kDa, respectively, and collecting the filtrate. In certain aspects, the method further comprises lyophilization of the fraction having proteins of about 3.5 to about 30 kDa.

Particular specific aspects provide a process for preparing a thymus extract composition, comprising: homogenizing thymus tissue with aqueous homogenization fluid to produce an aqueous thymus homogenate; removing tissue debris from the aqueous thymus homogenate to produce a primary supernatant; concentrating the primary supernatant to produce a secondary supernatant; and denaturing and clarifying the secondary supernatant to produce a clarified supernatant. In certain embodiments, the method further comprises further clarifying of the clarified supernatant by high-speed centrifugation to produce a final clarified supernatant fraction. In particular embodiments, the method further comprises sterilizing the final clarified supernatant fraction to produce a sterile final clarified supernatant fraction. In certain implementations, sterilizing is achieved by passing the final clarified supernatant fraction through a membrane filter. In certain aspects, the initial ratio of thymus tissue to aqueous homogenization fluid is about 300 g wet weight, or about 340 ml wet volume, of thymus tissue to about 0.8 L of homogenization fluid. In certain aspects, removing tissue debris from the aqueous thymus homogenate is achieved by a combination of low-speed centrifugation and crude filtration. In particular embodiments, concentrating the primary supernatant is achieved by repeating (a) and (b) using the primary supernatant, in place of the aqueous homogenization fluid, for homogenizing additional thymus tissue. In certain aspects, denaturing and clarifying of the secondary supernatant is achieved by heat denaturation, followed by low-speed centrifugation and crude filtration to remove particulate matter.

Additional specific aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; concentrating the primary supernatant to produce a secondary supernatant; denaturing and clarifying the secondary supernatant to produce an intermediate supernatant; concentrating the intermediate supernatant to produce a concentrated intermediate fraction; fractionating the concentrated intermediate fraction to remove molecules having a molecular weight less than about 3.5 kDa to produce a fractionated intermediate fraction; and fractionating the fractionated intermediate fraction, based on molecular weight, to obtain a fraction having proteins of about 3.5 to about 30 kDa. In certain embodiments, the method further comprises adjusting at least one of the pH or ionic strength of the fraction having proteins of about 3.5 to about 30 kDa to a physiological or therapeutically compatible value, to produce a pH- or ionic strength-adjusted fraction. In particular implementations, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. In some aspects, the method further comprises sterilizing the pH-, or ionic strength-adjusted fraction to produce a sterile pH-, or ionic strength-adjusted fraction. In particular embodiments, sterilizing is achieved by passing the fraction through a membrane filter. In certain aspects, the initial ratio of thymus tissue to aqueous homogenization fluid is about 350 g wet weight of thymus tissue to about 0.7 L of homogenization fluid. In certain embodiments, removing tissue debris from the aqueous thymus homogenate is achieved by a combination of low-speed centrifugation and crude filtration. In certain aspects, concentrating the primary supernatant is achieved by repeating (a) and (b) using the primary supernatant, in place of the aqueous homogenization fluid, for homogenizing additional thymus tissue. In particular implementations, denaturing and clarifying of the secondary supernatant is achieved by heat denaturation, followed by low-speed centrifugation and crude filtration to remove particulate matter. In particular aspects, the intermediate supernatant is concentrated, wherein concentrating is achieved by lyophilizing the intermediate supernatant either to complete dryness followed by aqueous resuspension to about 500 ml/13.6 kg (30 lbs.) original wet tissue, or to a volume of about 10% of its original volume. In particular aspects, concentrating the intermediate supernatant involves concentrating and fractionating, and wherein the concentrating and fractionating is achieved by adding ammonium sulfate to the intermediate supernatant, followed by low-speed centrifugation and suspension of the resulting ammonium sulfate pellet in an aqueous solution. In certain embodiments, fractionating the concentrated intermediate fraction to remove molecules having a molecular weight less than about 3.5 kDa is achieved by dialysis of the concentrated intermediate fraction, followed by high-speed centrifugation to remove particulate matter. In particular aspects, fractionating the fractionated intermediate fraction, based on molecular weight, is achieved by passing the fractionated intermediate fraction consecutively through a first and a second membrane filter having exclusion limits of about 100 and about 30 kDa, respectively, and collecting the filtrate.

Additional aspects provide a pharmaceutical composition, comprising a thymus extract composition produced in accordance with one or more of the processes disclosed herein.

Methods of Treating:

The term "treating" refers to, and includes, reversing, alleviating, inhibiting the progress of, or preventing a disease, disorder or condition, or one or more symptoms thereof; and "treatment" and "therapeutically" refer to the act of treating, as defined herein.

A "therapeutically-effective amount" is any amount of any of the compounds utilized in the course of practicing the invention provided herein that is sufficient to reverse, alleviate, inhibit the progress of, or prevent a disease, disorder or condition, or one or more symptoms thereof.

According to particular aspects the methods comprise administration of a composition comprising at least one of Thyex-1-6A and -6B, as defined herein, in combination with (e.g., adjunctive therapy) administration of a macrophage stimulating agent.

According to particular aspects, a polysaccharide is used as preferred macrophage stimulating agent. In preferred aspects, the macrophage stimulating agent comprises a beta glucan. In particular embodiments, the beta glucan comprises at least one linkage selected from the group consisting of beta: 1,3; 1,4; and 1,6 glucan linkages. Preferably, the linkage is that of beta 1,3 glucan.

According to particular aspects the inventive Thyex compositions are used in adjunctive therapies with extracts of at least one of: *Paresis crepe* (aka cauliflower mushroom or hanabaritake) preparations comprising beta 1-3 glucan; *Lentinula edodes* (shitake; e.g., alkaline digest according to the procedure reported by Ohno et al. (Biol. Phar. Bull. 23 866-872, 2000), comprises beta 1-3 glucan and chitin; *Astralagas membranaceus; Scutellaria baicalensis; Lilium longiforum* (aka Easter lilly); and *Houttuynia cordata* extracts.

Additional aspects provide a pharmaceutical composition, comprising a thymus extract composition produced in accordance with one or more of the processes disclosed herein.

Combination therapies. Combination therapies are also encompassed by aspects of the present invention. For example, the inventive methods may further comprise administration of a therapeutically-effective amount of one or more anti-microbial agents, such as anti-viral agents, anti-bacterial agents, and anti-fungal agents. Examples of anti-viral agents include but are not limited to: combivir, boceprevir, abacavir, docosanol, aciclovir, didanosine, cidofovir, acyclovir, delavirdine, adefovir, amantadine, amprenavir, arbidol, darunavir atazanavir, atripla, zanamivir, and oseltamivir. Examples of anti-bacterial agents include but are not limited to: metronidazole, tinidazole, co-trimoxazole, cephamandole, ketoconazole, latamoxef, cefoperazone, amoxicillin, cefmenoxime, furazolidone, doxycycline and erythromycin Examples of anti-bacterial agents include but are not limited to: imidazoles, (eg., miconazole, ketoconazole, clotrimazole, econazole, bifonazole, butoconazole, fenticonazole, isoconazole, oxiconazole, sertaconazole, sulconazole, and tioconazole), triazoles (eg., fluconazole, itraconazole, isavuconazole, ravuconazole, posaconazole, voriconazole, and terconazole), thiazoles (eg., abafungin), allylamines (eg., terbinafine, amorolfine, naftifine, and butenafine), and echinocandins (eg., anidulafungin, caspofungin, and micafungin).

Methods for Preparation of *Houttuynia cordata* Extracts:

Additional embodiments of the present invention (see working EXAMPLE 10) provide methods for preparing therapeutic extracts (D-YXC-1 and D-YXC-2) from the medicinal herb *Houttuynia cordata* Thunb. The processes comprise aqueous extraction and distillation steps.

Methods for Treatment of Aging and Related Conditions, and Restoration of Athletic Vigor and Stamina:

According to additional aspects (see working EXAMPLE 9), the endocrine system is also involved in the aging process, and the inventive Thyex compositions have substantial utility for additionally affecting aspects of the endocrine system, and have utility for treatment of aging and related conditions, and restoration of athletic vigor and stamina.

Without being bound by mechanism, these observations are explained, at least in part, by implicating pituitary release of growth hormone. It should be noted that levels of growth hormone in pituitary remains constant regardless of age.

According to particular aspects, Thyex directs the hypothalamus to resume release of growth-hormone-releasing hormone, which apparently decreases as animal ages.

Therefore, as an athlete ages there is a loss of vigor and/or stamina. According to particular aspects, and without being bound by theory, Thyex treatment benefits athletes, and particularly athletes in their 30's and older, who can regain lost stamina, and improved recovery from stressful exercises, etc.

Yet further specific exemplary aspects, provide a method for treating aging or age-related conditions, comprising administering to a subject in need thereof a therapeutically-effective amount of a thymus extract composition produced in accordance with one or more of the processes disclosed herein. In certain embodiments, the age-related condition is at least one selected from the group consisting of arthritis, mobility deficits, impaired vigor, and loss of appetite.

Additional aspects provide a method for treating impaired physical vigor or aptitude, comprising administering to a subject in need thereof a therapeutically-effective amount of a thymus extract composition produced in accordance with one or more of the processes disclosed herein. In certain aspects, treating impaired physical vigor or aptitude is treatment of at least one selected from the group consisting of lost stamina, and impaired recovery from physical stress.

Preferred embodiments relates to a method for treating arthritis and age-related issues, comprising administering to a mammalian subject in need thereof an effective amount of a thymus extract composition produced in accordance with the methods recited herein, wherein effects of arthritis and age-related issues is alleviated. In further preferred embodiments, the mammalian subject in need of treatment includes but is not limited to canine, feline, bovine, porcine, equine, ovine, and other large animals. In yet further preferred embodiments, the method for treating arthritis and age-related issues includes veterinary applications. In additional preferred embodiments, the veterinary applications include but are not limited to treating canine, feline, bovine, porcine, equine, ovine, and other large animals.

Methods for Treatment of Allergy and/or Autoimmune Disease:

According to additional aspects (see working EXAMPLE 11), the inventive Thyex compositions are used to treat individuals with allergy and autoimmune disorders (lichen sclerosis set atrophicus, rheumatoid arthritis, psoriasis, progressive systematic scleroderma, lupus, and juvenile diabetes).

Without being bound by theory, the mechanism likely comprises stimulation of suppressor T cells, which direct B cells producing the allergy antibodies to stop continued activity and control of reactive T cells.

Methods for Post-Surgical Treatment and/or Wound Healing:

According to additional aspects (see working EXAMPLE 12), the inventive Thyex compositions are used in post-surgical treatment, and/or for improved wound healing.

Methods for Treatment of Emphysema:

According to additional aspects (see working EXAMPLE 13), the inventive Thyex compositions are used in the Treatment of emphysema.

Methods for Treatment of PRRS, PRRS-Related Conditions and Secondary Infections:

According to additional aspects (see working EXAMPLES 15-17), the inventive Thyex compositions are used in the Treatment of PRRS, PRRS-related conditions and secondary infections (e.g., diarrhea, pneumonitis and/or intestinal disorders), and wasting syndrome in pregnant gilts and sows, and in swine being fattened for slaughter. According to particular aspects, adjunct treatment of swine with Thyex compositions is effective to enhance the efficacy of vaccine regimens in protecting PRRSV-susceptible reproductive systems against virulent field strains of PRRSV.

According to particular aspects, adjunct treatment of swine with Thyex compositions is effective to enhance protective immunity to PRRSV infection, even during late gestation.

According to further aspects, adjunctive treatment of swine with Thyex compositions is effective to enhance the efficacy of vaccine regimens in protecting PRRSV-susceptible respiratory systems against PRRSV and PRRSV-related conditions.

According to yet further aspects, adjunctive treatment of swine with Thyex compositions is effective to reducing vaccine-induced reproductive failure when such vaccines are administered during gestation (including late gestation), allowing for the use of less attenuated and/or more broadly protective vaccines.

Additional aspects provide a method for treating or preventing PRRS, PRRS-associated conditions or secondary infection, and wasting syndrome in an affected or susceptible swine in need thereof, comprising administering to the swine a therapeutically-effective amount of a thymus extract composition produced in accordance with one or more of the processes disclosed herein. In certain aspects the method further comprises administering an anti-microbial agent in combination with administration of the thymus extract composition. In particular implementations, the anti-microbial agent is an antibiotic or a *Houttuynia cordata* extract composition.

Further aspects, provide a method for treating or preventing, virus infection, virus-associated conditions or secondary infection, or wasting syndrome in an affected or susceptible swine in need thereof, comprising administering to the swine a therapeutically-effective amount of a thymus extract composition produced in accordance with one or more of the processes disclosed herein as an adjunct treatment in combination with administration of a vaccine element or regimen. In certain aspects the method further comprises administering an anti-microbial agent in combination with administration of the thymus extract composition. In particular implementations, the anti-microbial agent is an antibiotic or a *Houttuynia cordata* extract composition. In particular aspects, the vaccine element or regimen is based on one or more strains of Arteriviridae family viruses (e.g., comprises a PRRSV strain, wherein the PRRSV strain is selected from the group consisting of strains of PRRSV of either European and North American serotype, VR-2332 and Lelystad virus strains, NADC-8, NADC-9, and NVSL-14 strains, modified PRRSV strains, attenuated PRRSV strains, and combinations thereof). In certain aspects, the vaccine element is a monovalent, bivalent or polyvalent PRRSV-based vaccine, or an immunogenic or antigenic component of a PRRSV strain, or a modified or attenuated form of a PRRSV strain or PRRSV immunogen.

Yet additional aspects provide a method for treating or preventing vaccine-induced reproductive failure in a swine in need thereof, comprising administering to the swine a therapeutically-effective amount of a thymus extract composition produced in accordance with one or more of the processes disclosed herein as an adjunct treatment in combination with administration of a vaccine element or regimen. In certain embodiments, the method further comprises administering an anti-microbial agent in combination with administration of the thymus extract composition.

Methods for Treatment of Nausea and/or Vomiting Using Heat-Distilled *Houttuynia cordata* Extract.

According to additional aspects (see working EXAMPLES 10 and 17-20), the inventive heat-distilled *Houttuynia cordata* extract is useful in the treatment of nausea and/or vomiting in an affected or susceptible subject in need thereof, comprising administering to the subject a therapeutically-effective amount of a heat-distilled *Houttuynia cordata* extract composition produced in accordance with one or more of the processes disclosed herein. In certain aspects, the method further comprises administering an additional anti-nausea and/or anti-emetic agent in combination with administration of the heat-distilled *Houttuynia cordata* extract composition. In further aspects, the method comprises administering an additional anti-nausea and/or anti-emetic agent sequentially with administration of the heat-distilled *Houttuynia cordata* extract composition. In yet further aspects, the method comprises administering an additional anti-nausea and/or anti-emetic agent at a similar time with administration of the heat-distilled *Houttuynia cordata* extract composition.

According to additional aspects (see working EXAMPLES 10 and 17-20), the inventive heat-distilled *Houttuynia cordata* extract is useful in the treatment of nausea and/or vomiting brought on by any condition including, but not limited to pregnancy (e.g., morning sickness), motion sickness, gastrointestinal obstruction, peptic ulcer, drug toxicity, myocardial infarction, renal failure, and hepatitis. In addition, nausea and/or vomiting can be the side effect of many cancer treatments, including but not limited to chemotherapeutic drugs, radiation, and surgery.

According to further aspects, the inventive heat-distilled *Houttuynia cordata* extract has substantial utility to treat nausea in both humans and animals caused by illnesses, infections, or other treatments, and in particular embodiments is used in combination with one or more of the inventive Thyex compositions, plus or minus standard chemotherapy drugs, for the treatment of cancer.

In further aspects the method further comprises administering the heat-distilled *Houttuynia cordata* extract composition with a standard chemotherapy drugs, for the treatment of cancer. Standard chemotherapeutic drugs are well known in the art. In yet further aspects the method comprises administering the heat-distilled *Houttuynia cordata* extract composition in combination with a chemotherapeutic agent, wherein the administration can occur simultaneously, sequentially, or as needed to relieve nausea and vomiting symptoms.

Compositions:

Additional embodiments provide compositions produced in accordance with said processes. The Thyex-1, -2, -3, -4, -5, -6A and -6B composition embodiments are produced in accordance with the corresponding Thyex-1-6A and -6B processes (Working EXAMPLES 1-8). Likewise, the inventive heat-distilled *Houttuynia cordata* extract (D-YXC-1 and 2) composition embodiments are produced in accordance with the corresponding D-YXC-1, and 2 processes (EXAMPLE 10).

Methods of Treatment:

Further embodiments provide methods for the treatment of impaired physical vigor and stamina, and age-related disorders, comprising: utilizing thymus extract compositions alone, or in combination with a macrophage stimulating agent (see working EXAMPLE 9 below).

Treatment in Humans with Thyex-1-6A and 6B Compositions, with and without Macrophage Stimulating Agents.

Thyex-1-3 processes. EXAMPLES 1-3 provide exemplary process embodiments used for preparing Thyex-1-3, produced in accordance therewith suitable for oral delivery. Alternatively, Thyex-1-3 are lyophilized, stored at ambient temperature and reconstituted with sterile water prior to use.

Thyex-4 process. Steps (1)-(11) of EXAMPLE 4 comprise a process embodiment for producing Thyex-4 (step (12) relates to storage), suitable for oral delivery. Alternatively, Thyex-4 is lyophilized, stored at ambient temperature and reconstituted with sterile water prior to use.

Thyex-5 process. Steps (1)-(13) EXAMPLE 5 comprise a process embodiment for producing Thyex-5 (step (14) relates to storage), suitable for oral delivery. Alternatively, Thyex-5 is lyophilized, stored at ambient temperature and reconstituted with sterile water prior to use.

Thyex-6A process. EXAMPLE 6 provides an exemplary process embodiment used for preparing Thyex-6A produced in accordance therewith suitable for oral delivery, or delivery as a topical ointment or by injection or inhalation. Alternatively, Thyex-6A is lyophilized, stored at ambient temperature and reconstituted with sterile water prior to use.

Thyex-6B process. EXAMPLE 7 provides an exemplary process embodiment used for preparing Thyex-6B produced in accordance therewith suitable for oral delivery, or delivery as a topical ointment or by injection or inhalation. Alternatively, Thyex-6B was lyophilized, stored at ambient temperature and reconstituted with sterile water prior to use.

Treatment in Swine with Thyex-1-3 Compositions, with and without Antimicrobial Agents.

In Swine, the treatment methods utilizing the Thyex-1, -2 and -3 composition embodiments comprise for example, intra-muscular or subcutaneous injections thereof into affected swine to treat the primary PRRSV infection. Reproductive and maturational deficits, including early-stage PRRS symptoms (e.g., lethargy, anorexia, elevated body temperatures of 103-104° F.), were effectively treated with the administration of Thyex-1 or 2 alone. Preferably, PRRSV-infected animals are treated with a either a three-day, or up to about a 7-day regimen consisting of daily injections (delivered either intramuscularly (IM) or subcutaneously (SQ)) of 1 ml Thyex-1 or 2 composition.

Thyex-1 and 2 treatments were supplemented with administration of antimicrobial agents (e.g., either antibiotics or D-YXC-1 or 2) for advanced PRRS stages characterized by local or systemic secondary infections, such as *pneumococ-* cus and *salmonella*. In these instances, the antimicrobial agent was generally co-administered (by injection) with either the Thyex-1 or 2 composition. For example, for Thyex-1 or 2 plus D-YXC-1 combination therapy, PRRSV-infected animals were treated with a either a three-day, or up to about a 7-day regimen consisting of daily injections (delivered either intramuscularly (IM) or subcutaneously (SQ)) of 1 ml Thyex-1 or 2 composition, in combination with administration of the antimicrobial agent (e.g., either antibiotics or D-YXC-1 or 2). Alternatively, combination dosage regimes that involved a one-day course of two or three 1 ml injections of Thyex-1 or 2 over the course of a single day, combined with a two- or three-day course of antimicrobial agent administration were found to be therapeutically effective.

The antimicrobial agent (e.g., antibiotic or D-YXC-2 extract) composition was co-administered, by oral delivery, with the above-described Thyex-1 or 2 dosage regimens when the late-stage secondary infection was gastrointestinal. For example, D-YXC-2 (5 ml for sucklings or weanlings, and up to 15 ml for adult swine) was orally administered three times daily for two or three days, in conjunction with Thyex-1 or 2 injections.

Treatment with Thyex-3. The treatment methods utilizing the Thyex-3 composition embodiment comprise oral delivery thereof into affected swine to treat the primary PRRSV infection. Early stages of PRRS, as was found with the Thyex-1 and 2 compositions, were effectively treated with the administration of the Thyex-3 composition alone. In this instance, about 15 ml of the Thyex-3 composition was delivered daily for 30 consecutive days. Preferably, the Thyex-3 compositions are standardized to a protein concentration of 2 mg/ml.

Thyex-3 treatment was supplemented with antimicrobial agents (e.g., antibiotics; or D-YXC-1 or 2 extracts, for pneumonitis/systemic vs. gastrointestinal, respectively) for advanced PRRS stages in the same manner and dosage regimens as described above for co-administration with the Thyex-1 and 2 treatments.

Compositions produced in accordance with the processes of the present invention can be administered to breeding gilts, sows, boars, sucklings or weaned piglets. Preferably, the compositions are administered to breeding females before mating, or to pregnant animals to help protect the entire pregnancy period. Preferably, the compositions are administered to young sucklings and weanlings to protect their late nursery, grower and finishing stages.

Treatment of Thyex-1, 2, or 3 in combination with vaccines for preventing PRRSV infection. The inventive compositions are useful in adjunct therapies, and for this purpose are administered in relation to administration of PRRSV vaccine elements or vaccination regimens, to enhance vaccine efficacy. Such vaccines or vaccine elements include any administrable agent that is capable of promoting or enhancing a PRRSV-protective immune response in animals inoculated with the vaccine or vaccine element. PRRSV vaccines or vaccine elements are well known in the art (see "Background," herein above) and include, but are not limited to attenuated, "modified-live" or inactivated viruses or viral elements, viral antigens, monovalent (based on a single PRRSV strain), bivalent or even polyvalent vaccines (based on 2 or 3 strains; see, e.g., U.S. Pat. No. 5,976,537), various adjuvants, and combinations thereof, and may correspond to one or more genetically diverse field strains of PRRSV.

Adjunct therapy comprises administration of the inventive Thyex, and/or Thyex plus antimicrobial agent (e.g., antibiotic, or *Houttuynia cordata* extract) to swine at or about the time of initial vaccination and/or of subsequent vaccine boosts.

Therapeutic Utility of Thymus Extracts for The Treatment of PRRS. The treatment methods involving administration of Thyex-1, 2 or 3, alone or in combination with antimicrobial agents, were effective for pregnant gilts and sows, and for swine being fattened for slaughter (see Example 3, below). Post-farrowing gilts or sows showed a more rapid return to estrus and a higher pregnancy rate. Moreover, the treated animals recovered more rapidly, relative to non-treated control animals, from PRRS-associated secondary infections, such as pneumonia or *salmonella*.

Treated PRRSV-infected animals, in contrast to non-treated PRRS-V infected animals, had healthy appetites and reached full maturity within the same time period "on feed" as control animals that were not infected with PRRSV.

According to the present invention, adjunctive treatment of swine with Thyex (or Thyex plus antimicrobial agent) compositions enhances protective immunity to PRRSV, even during late gestation.

According to the present invention, adjunctive treatment of swine with Thyex (or Thyex plus antimicrobial agent) compositions enhances the efficacy of vaccine regimens in protecting PRRSV-susceptible respiratory systems against PRRSV.

According to the present invention, adjunctive treatment of swine with Thyex (or Thyex plus antimicrobial agent) compositions reduces vaccine-induced reproductive failure when such vaccines are administered during gestation, including late gestation.

Dose Determinations

A therapeutically-effective dose of a composition of the present invention refers to that amount of the composition sufficient to prevent or inhibit the effects of the treated condition, or to that amount sufficient to enhance the efficacy of adjunctive regimens. This amount may vary somewhat among subjects, but are nonetheless reasonably determined by one of ordinary skill within the art in view of the many art-recognized symptoms associated with the treated conditions.

Therapeutically-effective doses of the disclosed compositions are administered alone or in combination with other therapeutic agents, such as macrophage stimulating agents, anti-microbial agents (e.g., antiviral, antifungal or antibacterial agents), or are administered as adjunctive therapy in combination with administration of other treatment regimens.

In particular aspects, as in the Examples herein, the Thyex compositions are standardized at a protein concentration about 2 mg/ml. Preferably, the daily dose range for Thyex administration by injection is from about 0.05 mg/kg to about 1 mg/kg. More preferably, the dose range for Thyex administration by injection is from about 0.05 mg/kg to about 0.5 mg/kg. Even more preferably, the dose range for Thyex administration by injection is from about 0.1 mg/kg to about 0.4 mg/kg. Most preferably, the dose range for Thyex administration by injection is from about 0.2 mg/kg to about 0.3 mg/kg.

In particular aspects, the daily dose range for Thyex oral administration is from about 1 mg/kg to about 20 mg/kg. More preferably, the dose range for Thyex oral administration is from about 1 mg/kg to about 10 mg/kg. Even more preferably, the dose range for Thyex oral administration is from about 3 mg/kg to about 9 mg/kg. Most preferably, the dose range for Thyex oral administration is from about 5 mg/kg to about 8 mg/kg.

In particular aspects, the daily dose range for adjunctive administration of beta glucan can be determined by routine optimization by one of ordinary skill in the art. In particular aspects, the daily dose range for adjunctive administration of the polysaccharide extract (e.g., consisting of about 70% beta 1-3 glucan and 30% tissue proteins) will be about 300 to about 500 mg per day for a typical patient (e.g., or about 0.5 mg/kg to 15 mg/kg). In particular embodiments, using more highly purified polysaccharide fractions (e.g., void of protein; e.g., extracted by the method of Ohno et al (*Biol Pharm Bul,* 23, p 866, 2000), the daily dose will be about 300 mg per day (e.g., or about 0.5 mg/kg to 2.0 mg/kg) for a typical patient.

Preferably, as in the Examples herein, the inventive heat-distilled *Houttuynia cordata* extract (DYXC-1 and 2) compositions are standardized at a value of about 200 mg (dried herb wt equivalents; dhe)/ml.

Preferably, in terms of dried herb wt equivalents, the daily dose range for the inventive heat-distilled *Houttuynia cordata* extract (DYXC-1 and 2) administration injection is from about 5 mg/kg to about 50 mg/kg. More preferably, the dose range for the heat-distilled *Houttuynia cordata* extract (DYXC-1 and 2) administration by injection is from about 10 mg/kg to about 40 mg/kg. Even more preferably, the dose range for the heat-distilled *Houttuynia cordata* extract (DYXC-1 and 2) administration by injection is from about 15 mg (dhe)/kg to about 30 mg (dhe)/kg. Most preferably, the dose range for the heat-distilled *Houttuynia cordata* extract (DYXC-1 and 2) administration by injection is from about 20 mg (dhe)/kg to about 25 mg (dhe)/kg.

Antibiotic dosages were those of the label, according to the particular antibiotic used.

Formulations and Use

In particular preferred aspects, Thyex-1-6A and -6B have substantial utility in methods for treatment of various Human and mammalian conditions including, but not limited to impaired physical vigor or aptitude, and aging and/or age-related conditions (arthritis, mobility deficits, loss of appetite, etc.), comprising administration of said compositions.

For administration by injection, the Thyex, and the heat-distilled *Houttuynia cordata* extract (DYXC-1 and 2) compositions of the present invention are preferably formulated in aqueous solutions with physiologically compatible buffered saline (e.g., phosphate buffered standard physiological saline; 0.85% NaCl).

For oral administration, the pharmaceutical Thyex and the inventive heat-distilled *Houttuynia cordata* extract (DYXC-1 and 2) compositions of the present invention may take the form of, for example, liquids, gels, syrups, slurries, and the like, prepared by conventional means with pharmaceutically acceptable excipients such as: binding agents (e.g., pre-gelatinized maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP)); fillers (e.g., lactose, sucrose, mannitol, or sorbitol, microcrystalline cellulose or calcium hydrogen phosphate); lubricants (e.g., magnesium stearate, talc or silica); disintegrants (e.g., potato starch, sodium starch glycolate, cross-linked polyvinyl pyrrolidone, agar, or alginic acid or a salt thereof such as sodium alginate); or wetting agents (e.g., sodium lauryl sulfate). Such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Additional oral administration of the inventive heat-distilled *Houttuynia cordata* extract (DYXC-1 and 2) compositions can be in the form of an effervescent tablet. Effervescent formulations are known in the art for various active ingredients and vitamins. These effervescent formulations generally include an agent which is capable of releasing $CO_2$, and an agent which induces the release of $CO_2$. Suitable agents capable of releasing $CO_2$ which are used include alkali metal carbonates or alkali metal bicarbonates, such as sodium carbonate and sodium bicarbonate. Alkaline earth metal carbonate formulations are mainly contained in mineral preparations. Suitable agents for inducing $CO_2$ release include edible organic acids, or their acidic salts, which are present in solid form and which can be formulated with the active ingredient and the other auxiliaries to provide granules or tablets, without premature evolution of $CO_2$. The active ingredients are either present in the effervescent formulation as readily soluble compounds, or they are solubilized by salt formation during the dissolution process.

For administration by inhalation, the Thyex and the heat-distilled *Houttuynia cordata* extract (DYXC-1 and 2) compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

The Thyex, and the heat-distilled *Houttuynia cordata* extract (DYXC-1 and 2) compositions of the present invention may be formulated for parenteral administration by injection by bolus injection or continuous infusion. Formulations for injection may be presented in unit dosage form in ampoules or in multi-dose containers, with optionally, with an added preservative.

Vaccines are either those commercially available, or those prepared according to art-recognized methods, and are of various forms, including conventional forms such as aqueous dispersions, oil emulsions, liposome compositions, lyophilized forms, etc. Vaccine compositions and vaccination regimens may comprise different adjuvants, emulsifiers, stabilizers, etc. Vaccines are administered by different routes, including but not limited to parenteral, intramuscular, intranasal, intratracheal, subcutaneous, cutaneous, percutaneous or intracutaneous routes, and combinations thereof.

Vaccines may be prepared, inter alia, as aqueous solutions, syrups, elixers, or tinctures, and the liquid formulations may include suspensions and/or emulsions.

Thyex-4 may be lyophilized and dispensed in "00" size gelatin capsules: Oral. Approximately 40% thymic polypeptides. According to particular aspects, Thyex-4 may be used for stimulation of immune functions (e.g., anti-aging), to cure allergy and certain autoimmune disorders (e.g. celiac disease); and for treating gout.

Thyex-5. In particular aspects, Thyex-5 (e.g., lyophilized; approximately 80% thymic polypeptides) is mixed with other extracts (e.g. extracts containing polysaccharides such as beta 1-3 glucan). The mixtures, for example, can be dispensed in "00" gelatin capsules, or alternatively, for example, in size "3" capsule if not mixed with other extracts.

Thyex 6A. In particular aspects, Thyex-6A (e.g., sterile liquid extract) can be used to generate aerosols (e.g. for treating pneumonia or emphysema). Alternatively, for example, ointments can be used when Thyex-6A is mixed with water-soluble ointment base for treating, for example, lichen sclerosis et atrophicus, and wounds.

Thyex 6B. In particular aspects, Thyex-6BA (e.g., sterile liquid buffered, and saline adjusted for injection; at least 99% pure) is used for veterinary and human uses, including, but not limited to veterinary uses including: arthritis, anti-aging; pneumonia; dust pneumonia (IV), single tumor mass, such as Cancer Eye (squamous cell carcinoma in white-faced Herefords); virus infections, such as distemper, PRRS, shipping fever, etc.; shock trauma; arthritis, etc., and Human uses including, but not limited to: autoimmune disorders (IV or SQ) such as type 1 diabetes, lupus, psoriasis, rheumatoid arthritis, etc.; senile dementia, etc.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

The injection-use formulations can be presented in unit-dose or multi-dose sealed containers, such as ampules and vials, and can be stored in a freeze-dried (lyophilized) condition requiring only the addition of the sterile liquid excipient, or the heat-distilled *Houttuynia cordata* extract (DYXC-1 and 2), immediately prior to use. Extemporaneous injection solutions and suspensions can be prepared from sterile powders, granules, and tablets. The requirements for effective pharmaceutical carriers for injectable compositions are well known to those of ordinary skill in the art. See, for example, Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., 622-630 (1986).

Formulations suitable for topical administration include lozenges comprising a heat-distilled *Houttuynia cordata* extract (DYXC-1 and 2) of the invention and optionally, an additional therapeutic and a flavor, usually sucrose and acacia or tragacanth; pastilles comprising a gas-enriched fluid and optional additional therapeutic agent in an inert base, such as gelatin and glycerin, or sucrose and acacia; and mouth washes or oral rinses comprising a gas-enriched fluid and optional additional therapeutic agent in a suitable liquid carrier; as well as creams, emulsions, gels, and the like.

Additionally, formulations suitable for rectal administration may be presented as suppositories by mixing with a variety of bases such as emulsifying bases or water-soluble bases. Suitable pharmaceutical carriers are described in Remington's Pharmaceutical Sciences, Mack Publishing Company, a standard reference text in this field.

The dose administered to a subject, especially an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the condition being treated. A suitable dose is that which will result in a concentration of the therapeutic composition in a subject that is known to affect the desired response.

The size of the dose also will be determined by the route, timing and frequency of administration as well as the existence, nature, and extent of any adverse side effects that might accompany the administration of the therapeutic composition and the desired physiological effect.

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

EXAMPLE 1

Preparation of Thymus Extracts Thyex-1

This example provides an exemplary process embodiment used for preparing thymus extracts, and compositions ("Thyex-1") produced in accordance therewith:

Thyex-1:

Thyex-1 process. The following steps (1)-(16) comprise a process embodiment for producing Thyex-1 (step (17) relates to storage) suitable for oral delivery:

(1) Homogenization of thymus tissue. Fresh "prime" (i.e., not fibrous or whitish in appearance) porcine or bovine thymus glands were frozen (e.g., overnight). The frozen glands were rinsed briefly in clean water and "dressed" by removal of any associated fibrous or connective tissue, fatty tissue, or lymph node tissue. The prime washed, dressed thymus glands were cut into small pieces (e.g., about 2" cubes using a sharp knife), and homogenized through the use of a food processor or other grinding apparatus (e.g., a meat grinder). For homogenization, a volume of approximately 700 ml of 0.2% NaCl solution (in distilled water) was blended with approximately 350 g wet weight (about 400 ml wet volume) of cut-up thymus tissue in a standard size blender for at least one minute to produce a thymus homogenate;

(2) Low-speed Centrifugation. The "thymus homogenate" of step (1) was centrifuged at about 3,500×G for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Production of a "secondary filtered supernatant." Steps (1)-(3) were repeated with another 350 g wet weight (about 400 ml wet volume) of prime washed, dressed, cut-up thymus glands, except that the "primary filtered supernatant" of step (3) was used in place of the 700 ml of 0.2% NaCl solution of step (1). This substitution allowed for the production of a more concentrated (relative to the "primary filtered supernatant") secondary filtered supernatant;

(5) Heat denaturation. The "secondary filtered supernatant" of step (4) was heated to a temperature of about 75-80° C. by exposing the container thereof to a uniform heat source, such as a constant temperature water bath set at about 100° C., or a double boiler containing water at about 100° C. During said heating, the "secondary filtered supernatant" was frequently agitated or stirred until it reached about 75-80° C. to produce a heat-denatured secondary filtered supernatant;

(6) Low-speed Centrifugation. The "heat-denatured secondary filtered supernatant" of step (5) was centrifuged at 3,500×g for 5 minutes at ambient temperature to produce a pellet and a heat-denatured supernatant fraction;

(7) Production of a "heat-denatured filtered supernatant." The "heat-denatured supernatant fraction" of step (6) was decanted from the centrifugation pellets and gravity filtered through one or more layers of standard cheese cloth to produce a filtered, heat-denatured supernatant fraction (hereinafter the "intermediate supernatant" fraction) that was still slightly warm from the heat denaturation of step (5);

(8) Ammonium sulfate precipitation. About 650 gm of ammonium sulfate was added to 1 L of the warm "intermediate supernatant" of step (7). The solution was stirred until all the ammonium sulfate was dissolved, and then allowed to stand for about 1 hour at ambient temperature to produce a salted intermediate supernatant fraction;

(9) Low-speed centrifugation. The "salted intermediate supernatant" of step (8) was divided between two, 1 L centrifuge bottles and centrifuged at 3,500×g for 10 minutes at ambient temperature to produce ammonium sulfate pellets, and supernatant fractions;

(10) Suspension of ammonium sulfate pellet fraction. The "ammonium sulfate supernatants" from step (9) were decanted from the centrifugation tubes and discarded, and excess salt solution was carefully wiped from the inside tube walls. The two ammonium sulfate pellets of step (9) (i.e., corresponding to each 1-L centrifuge bottle) were then suspended and dissolved by gentle mixing with about 50 ml of 0.01 to 0.05 M phosphate buffer (about pH 7) for each pellet (alternatively, the pellets were suspended with distilled water). The suspensions were allowed to stand for about 1 hour at ambient temperature with brief agitation about every 15 minutes (to facilitate complete dissolution of the pellets) to provide an ammonium sulfate fraction. Note that dissolution of any remaining ammonium sulfate pellet can be affected by the step-wise addition of small amounts of distilled water (e.g., 5 ml aliquots), followed by agitation until the pellet is completely dissolved;

(11) Dialysis. The "ammonium sulfate" fraction of step (10) was transferred to clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C. to produce a dialyzed ammonium sulfate fraction. The distilled water was changed every 12 hours. Increasing hydrostatic pressure within the dialysis tubing was periodically relieved by removing some of the dialysate and transferring it to additional dialysis tubes;

(12) High-speed centrifugation. The "dialyzed ammonium sulfate fraction" of step (11) was centrifuged at 8,500×g for 10 minutes at ambient temperature to produce a pellet and dialyzed ammonium sulfate supernatant fraction;

(13) First exclusion-membrane filtration. The "dialyzed ammonium sulfate supernatant fraction" of step (12) was passed under nitrogen pressure at about 40-50 p.s.i. through a 100 kDa exclusion limit membrane filter (Amicon) at 4° C. (alternatively, ambient temperature will suffice) to produce a 3.5 kDa to 100 kDa filtrate;

(14) Second exclusion-membrane filtration. The "3.5 kDa to 100 kDa filtrate" of step (13) was passed under nitrogen pressure at 40 to 50 p.s.i. (275.8 to 344.75 Kpa, in metric units) through a 30 kDa exclusion limit membrane filter (Amicon) to produce a 3.5 kDa to 30 kDa filtrate;

(15) Adjustment of pH and ionic strength. About 5 ml of 1 M phosphate buffer (about pH 7) per liter was added to the "3.5 kDa to 30 kDa filtrate" of step (14). Solid NaCl was then added to 0.85% (weight to volume) to produce a pH- and ionic strength-adjusted 30 kDa filtrate, Thyex-1;

(16) Filter sterilization. The "Thyex-1" of step (15) was filter sterilized by passage through a 0.2µ membrane filter to produce sterile Thyex-1, suitable for oral delivery or delivery; and

(17) Storage. Thyex-1, produced in accordance with steps (1)-(16) of the Thyex-1 process, was typically stored frozen (e.g., −5° C. to −20° C.) in sterilized containers, and thawed just prior to use. According to particular aspects, the therapeutic activity of Thyex-1 was found to be stable to repeated freezing and thawing. Alternatively, Thyex-1 was lyophilized, stored at ambient temperature and reconstituted with sterile water prior to use.

According to particular aspects, one or more of the above steps are optional.

EXAMPLE 2

Preparation of Thymus Extracts Thyex-2

This example provides an exemplary process embodiment used for preparing thymus extracts, and compositions ("Thyex-2") produced in accordance therewith suitable for oral delivery:

Thyex-2:

Thyex-2 process. The following steps (1)-(8) comprise a process embodiment for producing Thyex-2 (step (9) relates to storage):

(1) Production of "intermediate supernatant." Steps (1)-(7) of the above-identified Thyex-1 process for the preparation of "intermediate supernatant" were followed (except that steps (1)-(3) were not repeated as in the Thyex-1 process) to produce an "intermediate supernatant" fraction;

(2) High-speed centrifugation. The "intermediate supernatant" fraction of step (1) was cleared (i.e., to remove potential pathogens) by centrifugation at 8,500×g for 10 minutes at ambient temperature to produce a pellet and a cleared intermediate supernatant fraction;

(3) Lyophilization. The "cleared intermediate supernatant" fraction of step (2) was lyophilized (i.e., freeze dried) either to complete dryness to produce a dried, cleared intermediate supernatant fraction, or until its volume was reduced by 90% to produce a lyophilized, cleared intermediate supernatant fraction;

(4) Dialysis. The "lyophilized, cleared intermediate supernatant," or the alternative completely "dried" fraction (suspended in 500 ml distilled water per 13.6 kg (30 lbs.) wet weight of thymus glands processed) of step (3) was dialyzed according to step (11) of the above-identified Thyex-1 process to produce a dialyzed, lyophilized intermediate supernatant fraction;

(5) High-speed centrifugation. The "dialyzed, lyophilized intermediate supernatant" of step (4) was centrifuged at 8,500×g for 10 minutes at ambient temperature to produce a pellet, and a cleared, dialyzed, lyophilized intermediate supernatant fraction;

(6) Exclusion-Membrane filtration. The "cleared dialyzed, lyophilized intermediate supernatant" of step (5) was passed consecutively under nitrogen pressure (40-50 p.s.i.) through 100 kDa and 30 kDa exclusion limit membrane filters (Amicon), according to steps (13) and (14) of the above-identified Thyex-1 process to produce a 3.5 kDa to 30 kDa filtrate. The protein concentration of the "30 kDa filtrate" was measured, and optionally diluted (typically, to about 2 mg/0.25 ml (lesser or greater dilutions were also made as desired);

(7) Adjustment of pH and ionic strength. The pH and ionic strength of the "3.5 kDa to 30 kDa filtrate" or the optionally diluted "3.5 kDa to 30 kDa filtrate" of step (6) was adjusted according to step (15) of the above-identified Thyex-1 process to produce a pH- and ionic strength-adjusted 3.5 kDa to 30 kDa filtrate, Thyex-2;

(8) Filter sterilization. The "Thyex-2" of step (7) was filter sterilized according to step (16) of the above-identified Thyex-1 process to produce sterile Thyex-2, suitable for oral delivery; and (9) Storage. Thyex-2, produced in accordance with steps (1)-(8) of the Thyex-2 process was typically stored frozen (e.g., −5° C. to −20° C.) in sterilized containers, and thawed just prior to use. According to particular aspects, the therapeutic activity of Thyex-2 was found to be stable to repeated freezing and thawing. Alternatively, Thyex-2 was lyophilized, stored at ambient temperature and reconstituted with sterile water prior to use.

According to particular aspects, one or more of the above steps are optional.

EXAMPLE 3

Preparation of Thymus Extracts Thyex-3

This example provides an exemplary process embodiment used for preparing thymus extracts, and compositions ("Thyex-3") produced in accordance therewith suitable for oral delivery:

Thyex-3:

Thyex-3 process. The following steps (1)-(10) comprise a process embodiment for producing Thyex-3 (step (11) relates to storage), suitable for oral delivery:

(1) Homogenization of thymus tissue. Fresh "prime" (i.e., not fibrous or whitish in appearance) porcine or bovine thymus glands were frozen (e.g., overnight). The frozen glands were rinsed briefly in clean water and "dressed" by removal of any associated fibrous or connective tissue, fatty tissue, or lymph node tissue. The prime washed, dressed thymus glands were cut into small pieces (e.g., about 2" cubes using a sharp knife), and homogenized through the use of a food processor or other grinding apparatus (e.g., a meat grinder). For homogenization, a volume of approximately 800 ml of 0.2% NaCl solution (in distilled water) was blended with approximately 300 g wet weight (about 340 ml wet tissue volume) of cut-up thymus tissue in a standard size blender for at least one minute to produce a thymus homogenate;

(2) Low-speed Centrifugation. The "thymus homogenate" of step (1) was centrifuged at about 3,500 rpm for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Production of a "secondary filtered supernatant." Steps (1)-(3) were repeated with another 175 g wet weight (200 ml wet tissue volume) of prime washed, dressed, cut-up thymus glands, except that the "primary filtered supernatant" of step (3) was used in place of the 800 ml of 0.2% NaCl solution of step (1). This substitution allowed for the production of a more concentrated (relative to the "primary filtered supernatant") secondary filtered supernatant;

(5) Production of a "tertiary filtered supernatant." Steps (1)-(3) were repeated with another 200 ml (wet volume) of prime washed, dressed, cut-up thymus glands, except that the "secondary filtered supernatant" from step (4) was used in place of the 800 ml of 0.2% NaCl solution of step (1). This substitution allowed for the production of a more concentrated (relative to the "primary" and "secondary" filtered supernatants") tertiary filtered supernatant;

(6) Heat denaturation. The "tertiary filtered supernatant" from step (5) was heated to a temperature of about 75-80° C. by exposing the container thereof to a uniform heat source such as a constant-temperature water bath set at about 100° C. or a double boiler containing water at about 100° C. During heating, the "tertiary filtered supernatant" was frequently agitated or stirred until it reached about 75-80° C. to produce a heat-denatured tertiary filtered supernatant fraction;

(7) Low-speed Centrifugation. The "heat-denatured tertiary filtered supernatant" fraction of step (6) was centrifuged at 3,500 rpm for 5 minutes at ambient temperature to produce a pellet and a heat-denatured supernatant fraction;

(8) Production of a "heat-denatured filtered supernatant." The "heat-denatured supernatant fraction" of step (7) was decanted from the centrifugation pellets and gravity filtered through one or more layers of standard cheese cloth to produce a filtered, heat-denatured supernatant fraction that was still slightly warm from the heat denaturation of step (6);

(9) High-speed centrifugation. The "filtered, heat-denatured supernatant" fraction of step (8) was centrifuged at about 8,500×g for 5 minutes at ambient temperature to produce a pellet, and a high-speed supernatant fraction, Thyex-3;

(10) Filter sterilization. The "Thyex-3" fraction of step (9) was filter sterilized according to step (16) of the above-identified Thyex-1 process to produce sterile Thyex-3, suitable for oral delivery; and

(11) Storage. Thyex-3, produced in accordance with steps (1)-(10) of the Thyex-3 process was typically stored frozen (e.g., −5 to −20° C.) in sterilized containers, and thawed just prior to use. According to particular aspects, the therapeutic activity of Thyex-3 was found to be stable to repeated freezing and thawing. Alternatively, Thyex-3 was lyophilized, stored at ambient temperature and reconstituted with sterile water prior to use.

According to particular aspects, one or more of the above steps are optional.

EXAMPLE 4

Preparation of Thymus Extracts Thyex-4

With reference to FIG. 4, this example provides an exemplary process embodiment used for preparing thymus extracts, and compositions ("Thyex-4") produced in accordance therewith suitable for oral delivery:

Thyex-4:

Thyex-4 process. The following steps (1)-(11) comprise a process embodiment for producing Thyex-4 (step (12) relates to storage), e.g., suitable for oral delivery (NOTE: the following steps (1)-(6) are referred to herein as "stage 1 steps (1)-(6)":

Stage 1 Steps (1)-(6):

(1) Homogenization of thymus tissue. Fresh "prime" (e.g., preferably not fibrous or whitish in appearance) porcine ovine or bovine thymus glands were frozen (e.g., overnight, or in some instances, preferably for at least 72 hours). The frozen glands were rinsed briefly in clean water and "dressed" by removal of any associated fibrous or connective tissue, fatty tissue, or lymph node tissue. The prime washed, dressed thymus glands were cut or minced into small pieces (e.g., about 1" to about 2" cubes using a sharp knife), and homogenized through the use of a food processor or other grinding apparatus (e.g., a meat grinder). For homogenization, a volume of approximately 700 ml of 0.2% NaCl solution (in distilled water) was blended for at least a minute with approximately 350 g wet weight of cut-up thymus tissue in a standard size blender to produce a thymus homogenate;

(2) Low-speed Centrifugation. The "thymus homogenate" of step (1) was centrifuged at about 3,500 rpm for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Heat denaturation. The "primary filtered supernatant" of step (3) was heated to a temperature of about 75-80° C. by exposing the container thereof to a uniform heat source, such as a constant temperature water bath set at about 100° C., or a double boiler containing water at about 100° C. During said heating, the "primary filtered supernatant" was frequently agitated or stirred until it reached about 75-80° C. to produce a heat-denatured primary filtered supernatant;

(5) Low-speed Centrifugation. The "heat-denatured primary filtered supernatant" of step (4) was centrifuged at 3,500×g for 5 minutes at ambient temperature to produce a pellet and a heat-denatured supernatant fraction;

(6) Production of a "heat-denatured filtered supernatant." The "heat-denatured supernatant fraction" of step (5) was decanted from the centrifugation pellets and gravity filtered through one or more layers of standard cheese cloth to produce a filtered, heat-denatured supernatant fraction (hereinafter the "intermediate supernatant" fraction) that was still slightly warm from the heat denaturation of step (4);

Stage 2 Steps (7)-(6):

(7) Dialysis. The "intermediate supernatant" fraction of step (6) was dialyzed according to step (11) of the above-identified Thyex-1 process (e.g., using clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C.) to produce a dialyzed, intermediate supernatant fraction;

(8) Low-speed Centrifugation. The "dialyzed, intermediate supernatant fraction" of step (7) was centrifuged at 3,500 rpm for 5 minutes at ambient temperature to produce a pellet and a heat-denatured supernatant fraction;

(9) Production of a "heat-denatured filtered supernatant." The "heat-denatured supernatant fraction" of step (8) was decanted from the centrifugation pellets and gravity filtered through one or more layers of standard cheese cloth to produce a filtered, heat-denatured supernatant fraction;

(10) High-speed centrifugation. The "filtered, heat-denatured supernatant" fraction of step (9) was centrifuged at about 8,500×g for 5 minutes at ambient temperature to produce a pellet, and a high-speed supernatant fraction, Thyex-4;

(11) Filter sterilization. The "Thyex-4" fraction of step (10) was filter sterilized according to step (16) of the above-identified Thyex-1 process to produce sterile Thyex-4, suitable for oral delivery; and

(12) Storage. Thyex-4, produced in accordance with steps (1)-(11) of the Thyex-4 process was typically stored frozen (e.g., −5 to −20° C.) in sterilized containers, and thawed just prior to use. According to particular aspects, the therapeutic activity of Thyex-4 is stable to repeated freezing and thawing. Alternatively, Thyex-4 was lyophilized, stored at ambient temperature and reconstituted with sterile water prior to use.

According to particular aspects, one or more of the above steps are optional.

EXAMPLE 5

Preparation of Thymus Extracts Thyex-5

With reference to FIG. 4, this example provides an exemplary process embodiment used for preparing thymus extracts, and compositions ("Thyex-5") produced in accordance therewith suitable for oral delivery:

Thyex-5:

Thyex-5 process. The following steps (1)-(13) comprise a process embodiment for producing Thyex-5 (step (14) relates to storage), suitable for oral delivery:

(1)-(6) (see Stage 1 steps (1)-(6) for Thyex-4 above);

(7) Ammonium sulfate precipitation. About 750 to about 800 gm of ammonium sulfate was added to 1 L of the warm "intermediate supernatant" of step (6). The solution was stirred until all the ammonium sulfate was dissolved, and then allowed to stand for about 1 hour at ambient temperature to produce a salted intermediate supernatant fraction;

(8) Low-speed centrifugation. The "salted intermediate supernatant" of step (7) was divided between two, 1 L centrifuge bottles and centrifuged at 3,500×g for 10 minutes at ambient temperature to produce ammonium sulfate pellets, and supernatant fractions;

(9) Suspension of ammonium sulfate pellet fraction. The "ammonium sulfate supernatants" from step (8) were decanted from the centrifugation tubes and discarded, and excess salt solution was carefully wiped from the inside tube walls. The two ammonium sulfate pellets of step (8) (i.e., corresponding to each 1-L centrifuge bottle) were then suspended and dissolved by gentle mixing with about 50 ml of distilled water (or optionally with 0.01 to 0.05 M phosphate buffer (about pH 7)) for each pellet. The suspensions were allowed to stand for about 1 hour at ambient temperature with brief agitation about every 15 minutes (to facilitate complete dissolution of the pellets) to provide an ammonium sulfate fraction. Note that dissolution, if desired, of any remaining ammonium sulfate pellet can be affected by the step-wise addition of small amounts of distilled water (e.g., 5 ml aliquots), followed by agitation until the pellet is completely dissolved;

(10) Dialysis. The "ammonium sulfate" fraction of step (9) was transferred to clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C. to produce a dialyzed ammonium sulfate fraction. The distilled water was changed every 12 hours. Increasing hydrostatic pressure within the dialysis tubing was periodically relieved by removing some of the dialysate and transferring it to additional dialysis tubes;

(11) High-speed centrifugation. The "dialyzed ammonium sulfate fraction" of step (10) was centrifuged at 8,500×g for 10 minutes at ambient temperature to produce a pellet and dialyzed ammonium sulfate supernatant fraction (Thyex-5);

(12) Adjustment of pH and ionic strength. Optionally, about 5 ml of 1 M phosphate buffer (about pH 7) per liter is added to the "dialyzed ammonium sulfate supernatant fraction of step (11). Optionally, solid NaCl is then added to 0.85% (weight to volume) to produce a pH- and ionic strength-adjusted dialyzed ammonium sulfate supernatant fraction (Thyex-5);

(13) Filter sterilization. The "Thyex-5" of step (12) was filter sterilized by passage through a 0.2μ membrane filter to produce sterile Thyex-5, suitable for oral delivery; and

(14) Storage. Thyex-5, produced in accordance with steps (1)-(13) of the Thyex-5 process, was typically stored frozen (e.g., −5° C. to −20° C.) in sterilized containers, and thawed just prior to use. According to particular aspects, the therapeutic activity of Thyex-5 was found to be stable to repeated freezing and thawing. Alternatively, Thyex-5 was lyophilized, stored at ambient temperature and reconstituted with sterile water prior to use.

According to particular aspects, one or more of the above steps are optional.

Above steps (7)-(11) are referred to herein as Stage 2 steps (7)-(11).

EXAMPLE 6

Preparation of Thymus Extracts Thyex-6A

Thyex-6A. With reference to FIG. 4, this example provides an exemplary process embodiment used for preparing thymus extracts, and compositions ("Thyex-6A") produced in accordance therewith suitable for oral delivery, or delivery as a topical ointment or by injection or inhalation:
Thyex-6A:

Thyex-6A process. The following steps (1)-(14) comprise a process embodiment for producing Thyex-6A (step (15) relates to storage), suitable for oral delivery:

(1)-(6) (see Stage 1 steps (1)-(6) for Thyex-4 and Thyex-5 above);

(7)-(11) (see Stage 2 steps (7)-(11) for Thyex-5 above);

(12) First exclusion-membrane filtration. The "dialyzed ammonium sulfate supernatant fraction" of step (11) was passed under nitrogen pressure at about 40-50 p.s.i. through a 100 kDa exclusion limit membrane filter (Amicon) at 4° C. (alternatively, ambient temperature will suffice) to produce a 3.5 kDa to 100 kDa filtrate;

(13) Second exclusion-membrane filtration. The "3.5 kDa to 100 kDa filtrate" of step (12) was passed under nitrogen pressure at 40 to 50 p.s.i. (275.8 to 344.75 Kpa, in metric units) through a 30 kDa exclusion limit membrane filter (Amicon) to produce a 3.5 kDa to 30 kDa filtrate (Thyex-6A);

(14) Filter sterilization. The "Thyex-6A" of step (13) was filter sterilized by passage through a 0.2μ membrane filter to produce sterile Thyex-6A, suitable for oral delivery, or delivery as a topical ointment or by injection or inhalation; and

(15) Storage. Thyex-6A, produced in accordance with steps (1)-(14) of the Thyex-6A process, was typically stored frozen (e.g., −5° C. to −20° C.) in sterilized containers, and thawed just prior to use. According to particular aspects, the therapeutic activity of Thyex-6A was found to be stable to repeated freezing and thawing. Alternatively, Thyex-6A was lyophilized, stored at ambient temperature and reconstituted with sterile water prior to use.

According to particular aspects, one or more of the above steps are optional.

EXAMPLE 7

Preparation of Thymus Extracts Thyex-6B

Thyex-6B process. With reference to FIG. 4, this example provides an exemplary process embodiment used for preparing thymus extracts, and compositions ("Thyex-6B") produced in accordance therewith suitable for oral delivery, or delivery as a topical ointment or by injection or inhalation:
Thyex-6B:

Thyex-6B process. The following steps (1)-(15) comprise a process embodiment for producing Thyex-6A (step (16) relates to storage), suitable for oral delivery, or delivery as a topical ointment or by injection or inhalation:

(1)-(6) (see Stage 1 steps (1)-(6) for Thyex-4, -5 and -6A above);

(7)-(11) (see Stage 2 steps (7)-(11) for Thyex-5 and -6A above);

(12) First exclusion-membrane filtration. The "dialyzed ammonium sulfate supernatant fraction" of step (11) was passed under nitrogen pressure at about 40-50 p.s.i. through a 100 kDa exclusion limit membrane filter (Amicon) at 4° C. (alternatively, ambient temperature will suffice) to produce a 3.5 kDa to 100 kDa filtrate;

(13) Second exclusion-membrane filtration. The "3.5 kDa to 100 kDa filtrate" of step (12) was passed under nitrogen pressure at 40 to 50 p.s.i. (275.8 to 344.75 Kpa, in metric units) through a 30 kDa exclusion limit membrane filter (Amicon) to produce a 3.5 kDa to 30 kDa filtrate (Thyex-6B);

(14) Adjustment of pH and ionic strength. Optionally, about 5 ml of 1 M phosphate buffer (about pH 7) per liter is added to the "dialyzed ammonium sulfate supernatant fraction of step (13). Optionally, solid NaCl is then added to 0.85% (weight to volume) to produce a pH- and ionic strength-adjusted dialyzed ammonium sulfate supernatant fraction (Thyex-6B);

(15) Filter sterilization. The "Thyex-6B" of step (14) was filter sterilized by passage through a 0.2μ membrane filter to produce sterile Thyex-6B, suitable for oral delivery, or delivery as a topical ointment or by injection or inhalation; and

(16) Storage. Thyex-6B, produced in accordance with steps (1)-(15) of the Thyex-6B process, was typically stored frozen (e.g., −5° C. to −20° C.) in sterilized containers, and thawed just prior to use. According to particular aspects, the therapeutic activity of Thyex-6B was found to be stable to repeated freezing and thawing. Alternatively, Thyex-6B was lyophilized, stored at ambient temperature and reconstituted with sterile water prior to use.

According to particular aspects, one or more of the above steps are optional.

EXAMPLE 8

General Considerations for Practice of the Above-Identified Thyex 1-6A and -6B Process Embodiments This Example 8 provides general considerations for practice of the above-identified
Thyex 1-6A and -6B process embodiments.

The above-described embodiments (Thyex-1 (steps 1-16), Thyex-2 (steps 1-8), Thyex-3 (steps 1-10), Thyex-4 (steps 1-11), Thyex-5 (steps 1-13), Thyex-6A (steps 1-14) and Thyex 6B (steps 1-15)), and the storage (e.g., lyophilization) steps of the inventive processes may be practiced with various modifications (including but not limited to those outlined below) that are within the scope of the present invention, and with alternatives or substitutions that will be recognized by those of ordinary skill in the art as being equivalent to those used herein to produce Thyex 1-6A and -6B.

Thymus glands. In particular aspects, animals (e.g., steers) are taken to a packing house at about 12-14 months. The thymus gland at this age is grayish. As an animal ages, the gland begins to become fibrous and even whitish in color. The optimum yield of final product from one kilogram (about 4.5 lb) of prime gland is 1 gram of purified Thyex (e.g., Thyex 6A or 6B). Sheep glands are generally from 6 month-old animals.

Freshly harvested thymus glands from porcine, ovine, or bovine sources should optimally be frozen within 24 hours of harvest and stored frozen, preferably for at least 72 hours. Freezing of the thymus glands renders the cells more susceptible to disruption in isotonic salt solution (e.g., 0.2% to 0.3% salt, such as NaCl) during homogenization. Variations in the freezing temperature and duration are within the scope of the present invention. The thymus glands are preferably frozen at least once (e.g., −5 to −20° C.) for production of optimal extracts.

For example, to process, thawed glands are preferably first washed and extraneous materials, such as fatty tissues, lymph nodes, and connective tissues are preferably excised and discarded. The tissues are preferably minced into approximately 1" squares before subjected to grinding (e.g., in a food processor, meat grinder, blender, or equivalent or suitable device). Preferably, the ground glands are homogenized in a blender at a proportion of about 350 gm wet weight with 700 ml of 0.2% saline for at least a minute. Following centrifugation (e.g., about 3,500×g for 10 minutes), the supernatant solution (upper and lower ppt discarded) is heat denatured by raising the solution temperature in a double boiler with constant stirring to a temperature in the range of about 75° C. to 80° C. (preferably 75° C.). Following a second centrifugation at, e.g., the same speed but for 5 minutes, the supernatant solution is collected and precipitate (ppt) discarded. In particular embodiments, the glands for all Thyex processes 1, 2, 3, 4, 5, 6A, and 6B are processed through this phase in identical or very similar fashion.

Production of "secondary"- and "tertiary"-filtered supernatants, such as those described in step (4) of the Thyex-1 process embodiment, step (1) of the Thyex-2 process embodiment, or steps (4) and (5) of the Thyex-3 process embodiment, allows for more concentrated filtered supernatants (relative to the corresponding "primary"-filtered supernatants), thus reducing the amount of ammonium sulfate required (Thyex-1 process embodiment), or the lyophilization time required (Thyex-2 process embodiment) to process a given amount of thymus tissue. Generally, variations in the final protein concentrations (e.g., in the range of 1 to 7 mg/ml) of the various primary-, secondary- and tertiary-filtered supernatants reflect the average age of the animals from which thymus tissue is obtained. Preferably, the protein concentration of the tertiary-filtered supernatant is about 4 mg/ml.

A heat-denaturation step is integral to all of the above-described Thyex process embodiments, and facilitates precipitation and subsequent removal of relatively large, heat-labile proteins that have no utility in the claimed compositions or methods (see below). Variation in the volume of filtered supernatant fraction treated, in the final temperature of the heat-denaturation step (within the range of about 75° C. to about 80° C.), in the temperature of the uniform heat source (within the range of about 80° C. to about 100° C., preferably about 100° C.) and in the time period over which heating of the filtered supernatant fractions from initial to said final temperature takes place (generally within the range of about 5 to 20 minutes for a 1-liter volume of supernatant, but generally for lesser or greater periods of time when heating smaller or larger volumes, respectively) are within the scope of the present invention. Preferably, the supernatant is heated to the final temperature at a rate that is as rapid as possible whereby said rate, in combination with stirring, generally minimizes the occurrence of local supernatant temperatures (e.g., supernatant temperatures near the heat-transferring wall of the supernatant container) that exceed the desired final temperature.

Likewise, variations in the duration and frequency of stirring during said heating are within the scope of the present invention, and depend on the temperature of the constant-temperature heat source and the volume of supernatant being heated. Generally, both the duration and frequency of stirring increase with increasing supernatant volume or heat-source temperature. Constant stirring is also effective, and preferable when heating relatively large supernatant volumes.

Step (8) of the above-described Thyex-1 process embodiment, and step (7) of the above-described Thyex-5, -6A and -6B process embodiment involves protein concentration/fractionation by ammonium sulfate precipitation of the "intermediate supernatant" fraction. Most preferably, solid ammonium sulfate is added to attain high salt concentrations (e.g., in excess of about 0.7 gm/ml) with minimal dilution. Alternatively, this concentration/fractionation step is achieved by adding saturated ammonium sulfate solution. However, because dilution of the intermediate supernatant fraction is preferably minimized, this embodiment results in relatively lower final salt concentrations (e.g. of about 0.5 gm/ml or greater), and is thus less efficient in precipitating (and thereby recovering) desirable low molecular weight proteins. Nonetheless, according to particular aspects, the resulting Thyex compositions have activity in the claimed methods, albeit to a lesser degree. Moreover, the present invention also encompasses the use of combinations of saturated or sub-saturated ammonium sulfate solutions with solid ammonium sulfate.

A dialysis steps of the above-described Thyex process embodiments, allow any molecules of molecular weight less that about 3.5 kDa to pass through. Variation in the precise exclusion limit of the dialysis membrane is within the scope of the present invention. Generally, any dialysis membrane is acceptable provided that its exclusion limit (porosity) enables the retention of molecules having molecular weights of about 5 kDa or larger.

Additionally, variation in the precise exclusion limits of the filtration membranes used in membrane filtrations steps of the Thyex process embodiments are within the scope of the present invention. Generally, any such filtration membrane is acceptable provided that its exclusion limit (porosity) does not result in exclusion (i.e., removal from the final Thyex composition) of molecules having molecular weights equal to or smaller than about 15 kDa. For example, exclusion membranes that exclude molecules of about 20, 30 or 40 kDa or larger are useful in the practice of the present invention, but result in final Thyex compositions that are less active per mg of final protein, compared to those compositions prepared using an exclusion membrane the excludes proteins larger than about 15 kDa. Preferably, dialysis and filtration membranes are chosen such that the resulting Thyex compositions comprise proteins in the molecular weight range of about 5 to 14 kDa.

The process embodiments (e.g., Thyex-3) may further comprise fractionation, based on molecular weight, to obtain a final protein fraction having proteins of about 3.5 to about 30 kDa.

Many different types of membrane filters (e.g., cellulose acetate membranes; Millipore) are commercially available for use in filter sterilization procedures. Some commercially-available membrane filters are self contained and provided as pre-sterilized, disposable units. Other membranes are mounted in reusable membrane holders, and heat sterilized in an autoclave prior to use.

Preferably, the final Thyex 1-6A and -6B compositions are standardized at a protein concentration about 2 mg/ml, based on optical density at 260 and 280 nm. Preferred dosages are discussed herein above under "Dose Determinations."

The instant processes comprise steps to optimize protein compositions for therapeutic use. For example, the above-described Thyex 6A and Thyex 6B process embodiments are designed to provide therapeutic compositions suitable for delivery as a topical ointment or by injection or inhalation, and include ammonium sulfate precipitation/fractionation steps. Thyex-5 is prepared from a similar process but is somewhat less refined than Thyex-6A or Thyex-6B, and is designed to be preferably mixed in appropriate ratios with extracted lyophilized herbal sources and administered orally in, for example, filled gelatin capsules. The Thyex-4 process embodiment lacks ammonium sulfate precipitation step but provides for a sufficiently-concentrated composition after lyophilization. The resulting Thyex-4 composition is less refined in relative to those of Thyex-5 (and Thyex-6A and -6B) but is nonetheless suitably concentrated and formulated for efficacious oral delivery in both animals and humans.

EXAMPLE 9

Treatment of Aging and Related Conditions, and Restoration of Athletic Vigor and Stamina Using the Inventive Thyex Compositions and Combinations Thereof Overview. All mammals possess a thymus gland at birth. As an animal ages, the gland begins to become fibrous and progressively degenerates. In humans, the thymus gland continues to grow until about age 20 before degenerating, and by age 50, no trace of glandular tissue is present. The progressive loss of the thymus can be temporally correlated to with diminishing natural physical stamina, and increasing incidence of age-related disorders.

According to additional aspects, the endocrine system is also involved in the aging process, and the inventive Thyex compositions have substantial utility for additionally affecting aspects of the endocrine system, and have utility for treatment of aging and related conditions, and restoration of athletic vigor and stamina.

Viral Infections:

Particular observations relating to viral infections initially suggested Thyex modulation of the endocrine system. In one instance involving Weak Calf Syndrome, where afflicted newborn calves are too weak to rise/nurse and with mortality rate of over 95%, the treated animals were romping in about 72 hours after a first Thyex infection followed by a second injection of Thyex 48 hours later. According to particular aspects, the response could not be explained simply due to stimulation of the immune system.

Similar observations and responses were seen by Applicant in pups naturally infected with canine distemper virus, which causes nearly 100% mortality rate. The surviving animals do not grow nor develop in size equal to that of uninfected animals in both situations. However, in limited trials, regular scheduled injections with Thyex for both the afflicted calves and the afflicted pups resulted in the surviving young animals to begin growing again.

Aging:

With respect to aging, several old dogs were treated with Thyex at regular schedules and showed signs of regaining youthfulness indicators, such as partial or complete relief from arthritic pain, increase in appetite and mobility, and in the case of one dog with defined atrophy of the hind quarters possibly due to lack of "exercise" associated with arthritis, the animal's hind quarters were significantly 'filled' with muscle mass and the animal resumed daily jogging with its master.

According to additional aspects of the present invention, and without being bound by mechanism, these observations are explained, at least in part, by implicating pituitary release of growth hormone. While the levels of growth hormone in pituitary typically remains constant regardless of age, according to particular aspects, Thyex stimulates the hypothalamus to release growth-hormone-releasing hormone (which apparently decreases as animal ages), which in turn stimulates pituitary growth hormone production.

According to particular aspects, regular treatment with Thyex acts to restore endocrine functions. In particular embodiments, an increase/rise in libido was seen in women with ovarian tissues removed, and in elderly men. In additional aspects, old uncastrated male dogs treated with Thyex showed increased "mounting" tendencies.

The aging process has also linked to loss of a body's capacity to control formation of free radicals and xeronine, which plays a major role in repairing many cell dysfunctions. Without being bound by theory, Thyex administration may restore such deficiencies.

Athletes:

It is a well established fact that athletes injected with growth hormone have "restored" physical vigor, as expected in a young person but lost as one ages. Thymic hormone has been reported to affect the endocrine system (e.g., release of FSH and LH in thymectomized mice by pituitary resulting in production of testosterone/estrogen).

Applicants' observations indicate that Thyex directs the hypothalamus to release hormones, in turn directing the pituitary to release specific hormones such as growth hormone, causing the liver to produce somatomedins, which are key hormones for regulating growth, increased metabolism, etc.

In particular aspects, individuals beyond 25 years in age are able to demonstrate physical aptitude, including recovery from physical stress, comparable individuals in their late teens.

Therefore, as an athlete ages there is a loss of vigor and/or stamina. According to particular aspects, and without being bound by theory, Thyex treatment benefits athletes, and particularly athletes in their 30's and older, who can regain lost stamina, and improved recovery from stressful exercises, etc.

According to particular aspects of the present invention, administering the inventive Thyex compositions to stimulate T cells, along with a polysaccharide extract to stimulate macrophage achieves a most effective immune therapy response. In certain aspects, administration of Thyex alone is sufficient.

Beta glucans. Various investigators, including the present Applicant, have reported that administering BCG showed limited success for treatment. Due to various problems in using BCG, however, the Applicant has sought other alternative means to activate macrophage and to complement the inventive Thyex compositions.

According to particular aspects, polysaccharides, such as beta glucan consisting of complex sugars found in cell walls of yeasts and mushrooms, are a preferred agent in combination with the inventive Thyex compositions, and act synergistically in combating aging and other related conditions.

There are three forms of beta glucan based on the linkages of the complex sugars, and these are recognized as beta-1, 3 or 1,4, and 1,6 glucan. Most are in the form of 1,3 and 1,4, or 1,3 and 1,6, but the 1,3 form, which is most abundant in the fruiting bodies of certain mushrooms (e.g., *Sparassis crupa* or Cauliflower mushroom; or *Lentinula edodes* or shitake, etc.). Typically, marketing strategies relating to marketing glucan (typically from the cell wall of the common yeast) emphasize "enhanced the immune system," "increases antibody production," and "fight cancer."

A reference by Ohno, Miura, Nakajima, and Yadomae (2000, Biol. Phar. Bull. 23, 866-872) describes a procedure for extracting beta glucan from shitake mushroom. Recently, two firms in Japan have successfully cultured the cauliflower mushroom (aka Hanabaritake), and the Applicant has obtained cauliflower mushroom powder form from these firms.

According to particular aspects, a preferred polysaccharide comprises one or more of the beta glucans, including three types based on the linkages: 1-3, 1-4, and 1-6). A number of commercial beta glucan products are available with most being derived from the common yeast. According to particular aspects, however, the preferred sources are mushrooms; with shitake being most common because of its ready availability/source, and cauliflower mushroom (*Sparassis crupa*), which is preferred as it contains beta 1-3 glucans, but unfortunately has limited availability. Additionally, the shitake mushroom, which is most widely available, is reported to contain the 1-3 glucan and chitin.

According to particular aspects, an oral route of administration is favorable, possibly because the intestinal walls are sites containing large amounts of lymph nodes and thus T cells.

Additional Combination Agents and/or Therapies:

As indicated above, preferred aspects comprise treatment of aging using Thyex compositions in combination with other fungal and/or herbal preparations, including the following:

*Paresis crepe* (aka cauliflower mushroom or hanabaritake) preparations, comprising beta 1-3 glucan, can be used to stimulate macrophage in combination with the inventive Thyex compositions.

*Lentinula edodes* (shitake; e.g., alkaline digest according to the procedure reported by Ohno et al. (Biol. Phar. Bull. 23 866-872, 2000), comprises beta 1-3 glucan and chitin, and can be used for treating age-related illness in combination with the inventive Thyex compositions.

*Astralagas membranaceus* (*Scutellaria baicalensis, Houttuynia cordata*; hot water extract of ground herbs and secondary extraction by alkaline digest as above), stimulate macrophages, and can be used for treating age-related illness in combination with the inventive Thyex compositions.

*Lilium longiforum* (aka Easter lilly; to prepare extract, leaves are pre-frozen, blended (homogenized) in water, and boiled. The liquid extract centrifuged and the supernatant solution distilled (approximately one-half volume is collected)), can be used for treating age-related illness in combination with the inventive Thyex compositions.

*Houttuynia cordata* (as mentioned above) extracts from leaves (e.g., processed as described herein in Example 10) can be used for treating age-related illness in combination with the inventive Thyex compositions. According to particular aspects, DYXC has substantial utility to treat nausea in both humans and animals caused by illnesses, infections, or other treatments, and in particular embodiments is used in combination with one or more of the inventive Thyex compositions, plus or minus standard additional drugs.

EXAMPLE 10

*Houttuynia cordata* Extracts

Figure 5:
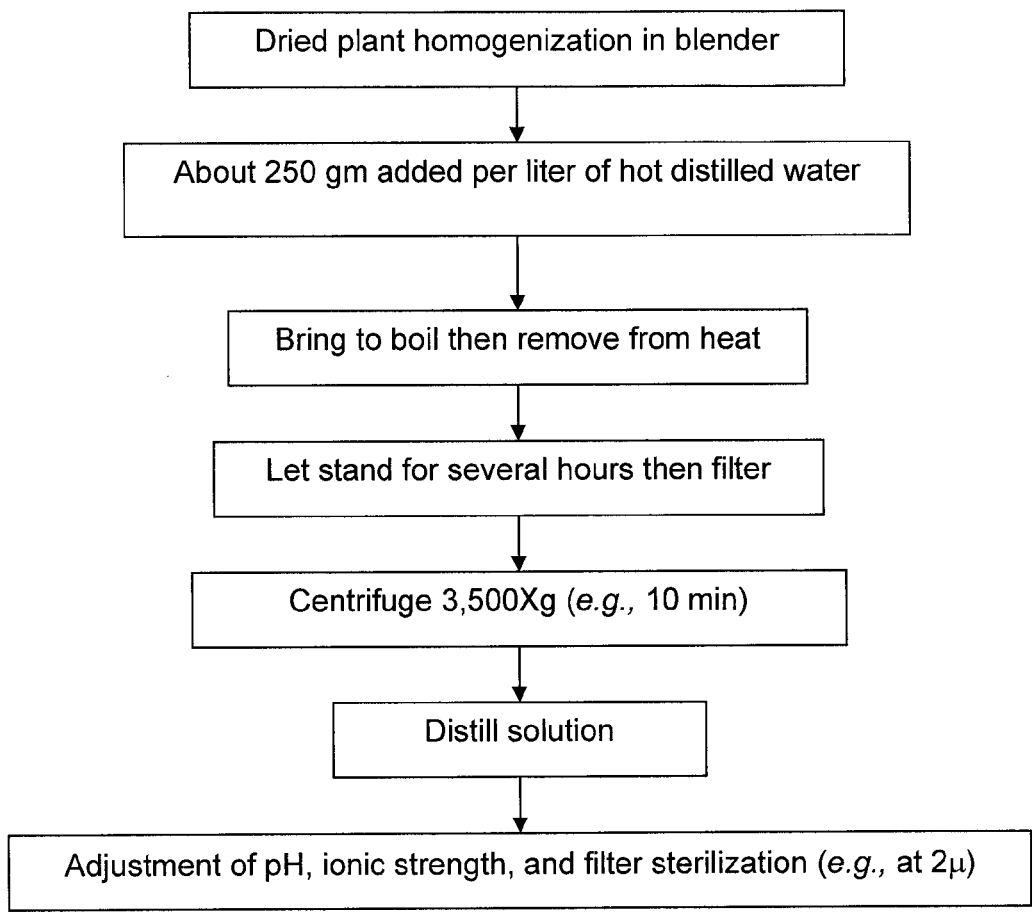
FIG. 5 is a flow diagrammatic representation comprising an inventive D-YXC process embodiment for preparing a *Houttuynia cordata* extract composition.

With reference to FIG. 5, this example provides two process embodiments used to prepare *Houttuynia cordata* extracts, and compositions ("D-YXC-1, and 2") produced in accordance therewith.

*Houttuynia cordata* Thunb, of the family Saururaceae, is a widely known herb (Houttuyniae) from ancient times, and its medicinal effects (particularly of the essential oils of the aerial parts thereof) have been described in various publications relating to herbal medicines (see, e.g., Huang, The Pharmacology of Chinese Herbs, CRC Press, 1999). The steam distillate prepared from fresh plants of *Houttuynia cordata* Thunb has been reported to have in vitro inhibitory activity against some, but not all, enveloped viruses (Hayashi et al., Planta Med. 61:237-241, 1995). The herb has also been reported to exhibit antibacterial activity (Huang, supra; Hu, Zentralbl. Veterinarmed. 44:365-70, 1997). The herb has been used as a tea for many years, but, as recognized in the art, the process of making the tea (e.g., grinding and boiling the *Houttuynia cordata*) produces a very bitter and unpleasant taste. There are many art recognized methods that attempt to reduce the bitterness of this aqueous extract of *Houttuynia cordata*, including organic extraction, roasting the herb, or bleach. Many groups have reported using pressurized organic solvent extraction to reduce the bitterness of hops.

According to particular aspects and as described in this Example, to reduce the bitterness and increase the palatability of the *Houttuynia cordata* extract, the *Houttuynia cordata* extract is subjected to further separation using centrifugation and heat-distillation. According to further aspects, it is this last step of heat-distillation that removes the majority of the bitterness and unpleasant taste associated with the *Houttuynia cordata* extract, and modifies it to a palatable extract suitable for oral administration. According to yet further aspects, this heat-distillation process not only provides for separation of the unpalatable and palatable portions, but also allows for separation of the anti-nausea and/or anti-emetic activity from the largely unpalatable portion. According to still further aspects, this heat-distillation process purifies and concentrates the anti-nausea and/or anti-emetic activity. According to certain aspects, the separation and/or removal of the bitterness from the aqueous extract and the separated aqueous extract using heat-distillation can be separation and/or can be a loss of the bitter flavor.

The commercially-available herb *Houttuynia cordata* Thunb was either grown locally or purchased from a Chinese herb shop (e.g., Star Import, Honolulu) for use in the following embodiments:

D-YXC-1 Process:

The following steps (1)-(7) comprise a process embodiment for producing D-YXC-1, suitable for oral delivery and in particular embodiments, for inhalation:

(1) Aqueous extraction. Fresh *Houttuynia cordata* or previously frozen *Houttuynia cordata* was immersed in a container of boiling water (454 g dried herb/5 L $H_2O$) and briefly stirred to disperse the herb. The container was immediately removed from the heat source, covered with a lid and the contents allowed to "steep" for about 8-10 hours (e.g., overnight) to produce an aqueous extract;

(2) Crude Filtration. The "aqueous extract" of step (1) was decanted from its container and gravity filtered through one or more layers of standard cheese cloth to produce a filtered aqueous extract. The steeped herb was compressed (e.g., by hand or mechanical means) to remove as much liquid as possible for filtration;

(3) Low-speed centrifugation. The "filtered aqueous extract" of step (2) was centrifuged (this is a preferred step to remove larger cellular debris, which facilitates subsequent steps) at 3,500×G for 10 minutes at ambient temperature to produce a pellet, and an aqueous supernatant fraction;

(4) Second Crude filtration. The "aqueous supernatant fraction" of step (3) was decanted from the centrifugation tubes and gravity filtered through one or more layers of standard cheese cloth to produce a filtered aqueous supernatant fraction;

(5) Distillation. The "filtered aqueous supernatant" fraction from step (4) was transferred to a standard distillation apparatus equipped with a temperature-controlled heating jacket (set at a temperature of slightly greater than about 100° C.) and a water-cooled condensation arm; Distillation was allowed to proceed until the volume of distillate was about half (i.e., about 2 L) that of the initial "filtered aqueous supernatant" volume to produce a distillate fraction (100 mL increments (from a 1000 mL sample) were tested for the presence of the bitter taste (described herein); after approximately 600 mL the bitter taste was detected no longer);

(6) Adjustment of pH and ionic strength. Phosphate buffer (of about pH 7) was added to the "distillate" fraction of step (5) to a final concentration of about 1 mM (e.g., by adding 1 ml of 1M phosphate buffer per liter of "distillate"). Solid sodium chloride was then added to a final concentration of about 0.85% (wt./volume) (e.g., to a concentration corresponding to "standard physiological saline") to produce a pH- and ionic strength-adjusted distillate fraction, D-YXC-1;

(7) Filter sterilization. The "D-YXC-1" fraction of step (6) was filter sterilized by passage through a 0.2μ membrane filter (Millipore) to produce sterile D-YXC-1, suitable for oral delivery or delivery by injection or inhalation; and (8) Storage. D-YXC-1, produced in accordance with steps (1)-(7) of the D-YXC-1 process, retained stable therapeutic activity when stored either at ambient temperature or refrigerated (e.g., 4° C.) in sterilized containers. In particular aspects, D-YXC-1 was dried or lyophilized, stored at ambient temperature and reconstituted (e.g., with sterile water or other suitable vehicle) prior to use.

D-YXC-2 Process:

The following steps (1)-(2) comprise a process embodiment for producing D-YXC-2, suitable for oral delivery, or for delivery by inhalation:

(1) Preparation of a distillate fraction. Steps (1)-(5) of the above-identified D-YXC-1 process were followed to produce a distillate fraction, D-YXC-2;

(2) Filter sterilization. The "D-YXC-2" fraction of step (1) was filter sterilized according to step (7) of the above-identified D-YXC-1 process to produce sterile D-YXC-2 suitable for oral delivery or delivery by inhalation (i.e., aerosol); and (3) Storage. D-YXC-2, produced in accordance with steps (1)-(2) of the D-YXC-2 process retained stable therapeutic activity when stored either at ambient temperature or refrigerated (e.g., 4° C.) in sterilized containers. In particular aspects, D-YXC-2 was dried or lyophilized, stored at ambient temperature and reconstituted (e.g., with sterile water or other suitable vehicle) prior to use.

General Considerations for Practice of the Above-Identified D-YXC-1 and 2 Process Embodiments:

The above-identified steps comprising embodiments of the D-YXC-1 (steps 1-7) and D-YXC-2 (steps 1-2) processes may be practiced with various modifications, including but not limited to those outlined below, that are within the scope of the present invention, and with alternatives or substitutions that will be recognized by those of ordinary skill in the art as being equivalent to those used herein to produce embodiments of D-YXC-1 and D-YXC-2.

The D-YXC-1 and D-YXC-2 embodiments of the present invention comprise aqueous extraction steps. Variations in the precise temperature and duration of the aqueous extraction steps are encompassed by the present invention. The fresh herb can optionally be cut-up or ground (e.g., blended in a commercial blender or grinder) to increase the extractable surface area. Additionally, the fresh herb can be frozen and thawed prior to blending to optimize the extraction process. Preferably, a ratio of about 250 gm dried plant tissue to about 1 L water is used, but the ratio is not critical and the amount of plant tissue may vary from about 100 to about 300 gm/L.

The above-described D-YXC-1 and D-YXC-2 embodiments comprise distillation steps. Variations in the nature of the heat source (e.g., temperature-controlled heating jacket, or steam distillation apparatus) or the precise temperature of heat source (within a range from about 100° C. to 102° C., where 100° C. represents the boiling point of water at sea level) and duration of the distillation steps will vary according to the precise distillation temperature and device used, and are within the scope of the present invention. Preferably, distillation is controlled by heating the solution at a temperature(s) within a range from 80° C. to 120° C. More preferably, distillation is controlled by heating the solution at a temperature(s) within a range from 90° C. to 110° C. Even more preferably, distillation is controlled by heating the solution at a temperature(s) within a range from 95° C. to 105° C. Most preferably, distillation is controlled by heating the solution at the lowest possible temperature that will still permit the solution to boil.

The above-described D-YXC-1 and D-YXC-2 embodiments comprise filtration steps. Variation in the mode of filtration or associated manipulations are within the scope of the present invention. For example, the "aqueous extract" or "aqueous supernatant fractions" corresponding to steps (1) and (3), respectively, of the D-YXC-1 process can optionally be frozen to induce precipitation (e.g., of unwanted starchy material) prior to the corresponding filtration and/or centrifugation steps (2), (3) and (4). Optionally, fresh *Houttuynia cordata* plants can be frozen for any length of time prior to processing. Optionally, this pre-freezing of fresh plants prior to processing (pre-boiling) assists in breaking and weakening of cell membranes and/or subsequent separation of materials (e.g., starch).

Preferably, the DYXC-1 and 2 distillate compositions are standardized (spectrophotometrically) at a value of about 200 mg (dried herb wt equivalents)/ml. Dosages are discussed herein above under "Dose Determinations."

In particular aspects, D-YXC-1 and 2 were dried or lyophilized, stored at ambient temperature and reconstituted (e.g., with sterile water or other suitable vehicle) prior to use.

According to particular aspects, the active anti-emetic factor contained within the extract is a very small molecule having a molecular weight of less than 1000 daltons, which is adsorbed rapidly and can block the vagus nerve from receiving stimuli due to pain, motion, infection, or as a complication attributed to certain medications (e.g., chemotherapy medications). According to additional aspects, treating nausea with *Houttuynia cordata* extract results in blockage of these stimuli and thus without further stimulation, the vomiting center in the region of the medulla oblongata is sedated.

According to further aspects, DYXC has substantial utility to treat nausea in both humans and animals caused by illnesses, infections, or other treatments, and in particular embodiments is used in combination with one or more of the inventive Thyex compositions, plus or minus standard chemotherapy drugs, for the treatment of cancer.

EXAMPLE 11

Treatment of Allergy and Autoimmune Disorders Using the Inventive Thyex Compositions In further aspects, the inventive Thyex compositions are used to treat individuals with allergy and autoimmune disorders (lichen sclerosis set atrophicus, rheumatoid arthritis, psoriasis, progressive systematic scleroderma, lupus, and juvenile diabetes).

Without being bound by theory, the mechanism may comprise stimulation of suppressor T cells, which direct B cells producing the allergy antibodies to stop continued activity and control of reactive T cells.

In additional aspects, Thyex has utility for treating (or preventing further deterioration of affected tissues/organs) in ALS, celiac disease, etc.

EXAMPLE 12

Post-Surgical Treatment and Wound Healing with Thyex Compostions

In further aspects, the inventive Thyex compositions are used in post-surgical treatment, and/or for improved wound healing.

Applicants have shown that animals in stress/shock will recovery within less than 30 minutes following injection with Thyex. Trials indicate that one undergoing surgery will recover much sooner if Thyex is administered the day of surgery and again at least one day later.

Without being bound by theory, the mechanism may comprise release of adrenalin from adrenal cortex. Furthermore, trials involving administering thyex on wounds have shown that wound healing was accelerated, and trials at a plastic surgery facility are underway to characterize the full benefits through the application of a Thyex ointment on the surgical wounds.

EXAMPLE 13

Treatment of Emphysema with Thyex Compositions

In further aspects, the inventive Thyex compositions are used in the Treatment of emphysema.

In further aspects of the present invention, ten patients in various stages of emphysema, but all requiring an oxygen support system, have gradually increased their respiratory capacity measurements through Thyex administration as an aerosol, with a reduction but not elimination of their dependence on oxygen support systems.

Without being bound by theory, the mechanism may comprise reduction of inflammation. If so, the accelerated wound healing described above may be due, at least partially, on this process.

EXAMPLE 14

Treatment of Swine with Thyex-1, 2 or 3 Compositions was Affective Against PRRS, and PRRS-Related Reproductive, Respiratory and Growth Disorders, Including Wasting Syndrome This example provides in vivo experiments and assays showing that treatment of PRRSV-infected animals with Thyex-1, 2 or 3, or combinations of Thyex-1, 2 or 3 with antimicrobial agents (e.g., antibiotics, or D-YXC-1 or 2) was affective against reproductive, growth and respiratory symptoms of PRRS. Specifically, Thyex-(or Thyex plus D-YXC-) treated gilts and sows returned to estrus more quickly and subsequently became pregnant more frequently than did non-treated control animals. Additionally, Thyex-(or Thyex plus D-YXC-) treated suckling and weaned pigs matured more rapidly, and spent less time with secondary conditions and infections (e.g., diarrhea and/or pneumonia) than did non-treated control animals (which either died or manifested characteristic 'wasting' syndrome).

Methods and Materials

Swine and disease status. Study group animals were obtained from a single farm swine herd ("test herd") that was clinically diagnosed with an endemic PRRSV infection. The PRRSV-positive status of the herd was confirmed by standard serological assays (IFA and c-ELISA) performed by the Animal Disease Diagnostic Laboratory, Washington State University, Pullman, Wash. Secondary symptoms displayed within the test herd included broncho-pneumonia, Salmonellosis, and diarrhea (especially among post weanlings).

Treatment groups, and data presentation. PRRSV-positive animals from the test herd were divided into "Thyex-1" treatment groups, "Thyex-1 plus antimicrobial agent (e.g., antibiotics or D-YXC-1)" combination treatment groups, and "control" groups that received neither Thyex-1 nor antimicrobial agent. An additional "reference" group consisting of corresponding uninfected swine was used to normalize data for presentation. Data are reported as a percentage of the corresponding uninfected reference group data.

Dosage regimens. Animals in the Thyex-1 treatment group were treated with either a three- or up to about a seven-day regimen consisting of daily injections, delivered either intramuscularly (IM) or subcutaneously (SQ), of 1 ml Thyex-1 composition (e.g., about 0.2 mg/kg/day to about 0.3 mg/kg/day). Animals in the Thyex-1 plus antimicrobial agent (e.g., antibiotics or D-YXC-1) combination therapy group received the same Thyex-injection regimens with the addition daily administration of antimicrobial agent (e.g., antibiotics or D-YXC-1). In the case of D-YXC-1 combination therapy, twice-daily injections, either IM or SQ, of D-YXC-1 (about 20 mg/kg/day to about 25 mg/kg/day), was administered. Antibiotic dosages were those of the label, according to the particular antibiotic used.

Results

Reproductive study. Pregnant gilts and sows from a PRRSV-infected swine herd were treated with either Thyex-1 or Thyex-1 plus antimicrobial agent (e.g., antibiotics or D-YXC-1), or were left untreated for controls. After farrowing and weaning, reproductive data (in the form of % of animals returning to estrus relative to an uninfected reference group, and in the form of % of animals pregnant relative to an uninfected reference group) was assessed for all three groups.

The data showed that post-farrowing gilts or sows treated with Thyex-1, or with a combination of Thyex-1 and antimicrobial agent (e.g., antibiotics or D-YXC-1), showed a significantly more rapid return to estrus and a higher pregnancy rate relative to non-treated, PRRSV-infected control animals. Additional studies showed that the Thyex-1 and 2, and the Thyex plus antimicrobial agent (e.g., D-YXC-1 and 2 compositions) were substantially equivalent and effective for treating these PRRS reproductive symptoms. Thyex-3 treatment was also found to be effective in this regard, but involved oral administration (about 15 ml/day) of the composition over longer treatment periods (e.g., 20-30 consecutive days). Preferably, for oral administration, the thyex-3 protein concentration was standardized at a protein concentration of about 2 mg/ml.

Maturation and respiratory study. Suckling and weanling swine from a PRRSV-infected swine herd were treated with either Thyex-1 or Thyex-1 plus antimicrobial agent (e.g., antibiotic or D-YXC-1 and 2 compositions), or were left untreated as controls. The animals were placed on feed, and maturation data (in the form of 'average daily gain' (ADG) or 'feed to gain' (FG) relative to an uninfected reference group), and respiratory data (in the form of the average time spent with respiratory symptoms relative to an uninfected reference group) was assessed for all three groups.

The data showed that weanling swine treated with Thyex-1, or with a combination of Thyex-1 and antimicrobial agent (e.g., D-YXC-1 and 2 compositions) matured more rapidly, and spent less time with secondary conditions and infections (e.g., pneumonia, intestinal disorders, and diarrhea) than did non-treated, PRRSV-infected control animals. The non-treated animals that survived the infection remained as runts (i.e., PRRSV-related "wasting" syndrome), whereas treated littermates continued to develop as those in the uninfected control animals. Thus, the inventive treatment was also found to be effective for treatment of wasting syndrome. As in the case of the reproductive studies, the Thyex-1 and 2, and the Thyex plus antimicrobial agent (e.g., antibiotics, or D-YXC-1 and 2) compositions were found to be substantially equivalent and effective for treating PRRSV-related maturation and respiratory symptoms, including diarrhea.

Thyex-3 treatment was also found to be effective in this regard, but involved oral administration (about 15 ml/day) of the composition to weanlings over longer treatment periods (e.g., 20-30 consecutive days). Preferably, for oral administration, the thyex-3 protein concentration was standardized at a protein concentration of about 2 mg/ml.

EXAMPLE 15

Thyex Compositions are Useful as Adjunct Methods for Vaccination Regimens in Swine Recent outbreaks of atypical or acute PRRS in vaccinated swine raise serious concern about the efficacy of current vaccines and provide impetus for developing more effective vaccines and/or other adjunct methods. For example, the current monovalent (based on a single PRRSV strain), bivalent or even polyvalent vaccines (based on 2 or 3 strains; see, e.g., U.S. Pat. No. 5,976,537) are not effective in protecting against infections of genetically diverse field strains of PRRSV that routinely infect "vaccinated" herds (Meng, Vet. Microbiol. 74:309-29, 2000). That is, strains are often poorly cross-protective. Moreover, "modified-live" vaccines cause large losses in gestating sows, so that their use is, at best, restricted to non-gestating sows (Dewey et al., Prev. Vet. Med. 40:233-241, 1999; Mengeling et al., Am J. Vet. Res. 60:796-801, 1999). Furthermore, substantially attenuated vaccines, while reducing the occurrence of vaccine-induced reproductive failure when pregnant sows are vaccinated, are likely to be less cross-protective than less attenuated versions.

Finally, PRRSV vaccine approaches, like eradication protocols, do not address the practical and financial realities associated with substantial swine groups that are already infected with diverse field strains of PRRSV, or with substantial vaccinated swine groups that will nonetheless still become infected with one or more diverse field strains of PRRSV.

Therefore, according to particular embodiments of the present invention, Thyex-1, 2 or 3, or combinations of Thyex-1, 2 or 3 with antimicrobial agents (e.g., antibiotics, or D-YXC-1 or 2) are useful as an adjunct therapy or method to enhance the efficacy of PRRSV vaccine elements and vaccination regimens. Specifically, Thyex-1, 2 or 3 alone, or in combination with antimicrobial agents is used as an adjunct treatment to significantly enhance the efficacy of vaccination of gilts and sows with various PRRSV vaccines.

Accordingly, a PRRSV vaccine (e.g., and attenuated PRRSV vaccine) is used to vaccinate uninfected gilts, in combination with the inventive adjunct Thyex treatment (e.g., with Thyex-1, 2 or 3, alone or in combination with antimicrobial agents, as disclosed herein). Such PRRSV vaccines are derived, for example, from PRRSV strains NADC-8, NADC-9, and NVSL-14, which normally cause reproductive failure in pregnant gilts. The vaccines are formulated in an effective immunization dosage with a pharmaceutically acceptable carrier or diluent, such as physiological saline or tissue culture medium. The "effective immunization dosage" is that amount needed to induce immunity in a pig against challenge by a virulent strain of PRRSV; typically $10^4$ to $10^6$ median cell culture infectious units ($CCID_{50}$) (virus is propagated in, e.g., primary alveolar macrophages, or in more generally available African green monkey kidney cell lines, such as MARC-145 cells or the MA-104 clone thereof, that are available at diagnostic laboratories nationally). Preferably, the vaccines are administered oronasally or by injection. Preferably, appropriate adjuvants may be included in the vaccine formulation. The vaccines are used individually, or are preferably combined together in the formulation of polyvalent vaccines.

In particular embodiments, gilts are vaccinated either within the first few weeks after birth, or at least 2 months prior to mating. The vaccine is preferably administered to gilts at least two months prior to mating to preclude vaccine-induced reproductive failure. Preferably, all pigs are vaccinated within the first few weeks after birth in order to protect against the respiratory symptoms of the disease. Animals are treated at or near the time of vaccination, for example, with either a two- or three-day injection regimen consisting of daily injections of 1 ml of Thyex-1 or 2 composition, delivered either intramuscularly (IM) or subcutaneously (SQ). Alternatively, animals are treated at or near the time of vaccination, for example, with either a two- or three-day injection regimen consisting of daily injections of 1 ml of Thyex-1 or 2 composition, delivered either intramuscularly (IM) or subcutaneously (SQ) in combination with the addition of twice-daily injections, either IM or SQ, of D-YXC-1 (5 ml/animal). Preferably, Thyex adjunct treatment occurs shortly before or at the time of vaccination.

Accordingly, adjunctive therapy with either Thyex-1, 2 or 3 compositions (or with Thyex-1, 2 or 3 plus antimicrobial agent) results in enhanced efficacy of PRRSV vaccination regimens, where the reproductive performance of vaccinated sows receiving the adjunct Thyex treatment exceeds that of corresponding vaccination only control groups. Moreover, fewer live-born pigs from vaccinated sows receiving Thyex adjunct therapy are infected at birth, compared to the live-born pigs from sows receiving vaccination only (no Thyex adjunct treatment).

According to the present invention, adjunct treatment of swine with Thyex (or Thyex plus antimicrobial agent) compositions enhances the efficacy of vaccine regimens in protecting PRRSV-susceptible reproductive systems against virulent field strains of PRRSV (including strains NADC-8, NADC-9, and NVSL-14), found in widely different geographical areas including Canada, Guatemala, and various states of the United States (Wesley et al., *Proc. Am. Assoc. Swine Pract.* 141-143, 1996; and see U.S. Pat. No. 5,976, 537).

According to the present invention, sows that are vaccinated in combination with administration of the inventive adjunct treatment show enhanced protective immunity to PRRSV, even during late gestation (e.g., at about Day 90 of gestation), the time of greatest reproductive susceptibility to PRRSV due to viral crossing of the placenta (Mengeling et al., *Am. J. Vet. Res.,* 57:834-839, 1996).

According to the present invention, adjunctive treatment of swine with Thyex (or Thyex plus antimicrobial agent) compositions enhances the efficacy of vaccine regimens in protecting PRRSV-susceptible respiratory systems against PRRSV and PRRSV-related disease, including that caused by a variety of virulent field strains of PRRSV.

EXAMPLE 16

Thyex Compositions are Useful as an Adjunct Treatment to Reduce or Preclude Vaccine-Induced Reproductive Failure in Swine Late gestation in swine (e.g., at about Day 90 of gestation) is the time of greatest reproductive susceptibility to PRRSV (attributed to viral crossing of the placenta; Mengeling et al., *Am. J. Vet. Res.,* 57:834-839, 1996), and thus corresponds to a period of great economic/commercial importance for the swine breeder.

Vaccination of pregnant swine during gestation is particularly problematic, because of the art-recognized problem of vaccine-induced reproductive failure. This problem can be partially addressed by the development of substantially attenuated virus strains for use in the preparation of vaccines to be administered during gestation (see, e.g., U.S. Pat. No. 5,976,537 to Mengeling et al, incorporated by reference herein in its entirety). However, development of such substantially attenuated PRRSV strains is expensive and time consuming, and can result in the production of less efficacious vaccines. Additionally, new PRRSV strain variants are frequently occurring in the field, and substantially attenuated vaccines are less likely to be cross-protective than less attenuated vaccines. Preferably, less attenuated and more broadly protective vaccines could be administered during gestation, if the associated vaccine-induced reproductive failure could be reduced or precluded.

According to the present invention, adjunctive treatment of swine with Thyex (or Thyex plus antimicrobial agent) compositions allows for the use of less attenuated more broadly protective vaccines by significantly reducing vaccine-induced reproductive failure when such vaccines are administered during gestation, including late gestation.

Therefore, the compositions and treatment methods of the present invention were effective for treating PRRS, PRRS-related conditions and secondary infections (e.g., diarrhea, pneumonitis and/or intestinal disorders), and wasting syndrome in pregnant gilts and sows, and in swine being fattened for slaughter. Post-farrowing gilts or sows showed a more rapid return to estrus and a higher pregnancy rate. Additionally, treated suckling and weanling swine recovered more rapidly, relative to non-treated control animals (which either died or manifested characteristic 'wasting' syndrome), from PRRS-associated secondary infections, such as pneumonia, and wasting syndrome. Treated sucklings and weanlings, in contrast to non-treated animals, had healthy appetites and reached full normal maturity within the same time period "on feed" as control animals that were not infected with PRRSV. Compositions produced in accordance with the processes of the present invention can be administered to breeding gilts, sows, boars, sucklings or weaned piglets. Preferably, the compositions are administered to breeding females before mating, or to pregnant animals to help protect the entire pregnancy period. Preferably, the compositions are administered to young sucklings and to young pigs shortly after weaning to protect their late nursery, grower and finishing stages.

According to particular aspects, adjunct treatment of swine with Thyex compositions is effective to enhance the efficacy of vaccine regimens in protecting PRRSV-susceptible reproductive systems against virulent field strains of PRRSV.

According to additional aspects, adjunct treatment of swine with Thyex compositions is effective to enhance protective immunity to PRRSV infection, even during late gestation.

According to further aspects, adjunctive treatment of swine with Thyex compositions is effective to enhance the efficacy of vaccine regimens in protecting PRRSV-susceptible respiratory systems against PRRSV and PRRSV-related conditions.

According to yet further aspects, adjunctive treatment of swine with Thyex compositions is effective to reducing vaccine-induced reproductive failure when such vaccines are administered during gestation (including late gestation), allowing for the use of less attenuated and/or more broadly protective vaccines.

EXAMPLE 17

*Houttuynia cordata* Extracts Had Substantial Use as an Anti-Nausea/Anti-Emetic Therapeutic in Mammals

*Houttuynia cordata* extracts (DYXC) were prepared as disclosed in Example 10. A canine patient presented with an acute gum lesion due to pyorrhea. In addition, blood samples indicated that the animal had a systemic infection and had acute dehydration due to frequently vomiting. A treatment regime of 2 cc of DYXC placed directly into mouth of the animal every hour was begun. The intense vomiting halted almost immediately and within three days the canine began to eat and drink normally. After seven days of treatment the acute gum lesion due to pyorrhea healed completely. The anti-nausea properties of the *Houttuynia cordata* extracts (DYXC) was confirmed through a number of other cases.

EXAMPLE 18

*Houttuynia cordata* Extracts Had Substantial Use as an Anti-Emetic Therapeutic in Humans

*Houttuynia cordata* extracts were prepared as disclosed in Example 10. A female human patient presented with severe nausea due to the chemotherapy treatment from her stomach cancer. The subject reported that the nausea was very taxing. About 30 cc of the *Houttuynia cordata* extract (DYXC) was administered to the subject (orally) as needed for treating the nausea. The subject reported rapid abatement of nausea.

Likewise, a male human cancer patient being treated with chemotherapy presented with severe nausea. About 30 cc of the *Houttuynia cordata* extract (DYXC) was administered to the subject (orally) as needed for treating the nausea. The subject reported rapid and substantial abatement of nausea within a few minutes after administration.

EXAMPLE 19

*Houttuynia cordata* Extracts has Substantial Use as Anti-Nausea/Anti-Emetic Therapeutics Animals (e.g., Vertebrates, Mammals, Etc.)

*Houttuynia cordata* extracts are prepared, for example, as disclosed in Example 10. According to certain aspects, the heat distilled extracts of *Houttuynia cordata* have substantial use in relieving nausea and/or vomiting. This nausea and/or vomiting can be due to any condition including, but not limited to pregnancy, motion sickness, gastrointestinal obstruction, peptic ulcer, drug toxicity, myocardial infarction, renal failure, and hepatitis. In addition, nausea and/or vomiting can follow the administration of many drugs particularly cancer chemotherapeutic agents. According to certain aspects, subjects presenting with nausea and/or vomiting find that these symptoms quickly abate upon treatment with the *Houttuynia cordata* heat distilled extracts (DYXC).

EXAMPLE 20

*Houttuynia cordata* Extracts are Further Fractionated to Identify the Anti-Nausea Agent As shown in Example 10, *Houttuynia cordata* extracts can be fractionated into portions that contain anti-nausea and/or anti-emetic activity. According to certain aspects, the heat distilled fraction (as disclosed in Example 10) can be further fractionated using separation techniques well known in the art (e.g., fractional distillation, centrifugation, chromatography, crystallization, electrophoresis, evaporation, extraction, flotation, flocculation, precipitation, and column chromatography). The further separated fractions can be screened for anti-nausea and/or anti-emetic activity as described herein. In addition and according to particular aspects, the further separated fractions can be screened for anti-nausea and/or anti-emetic activity using methods well known in the art (e.g., using test frogs and/or chicks). For example, researchers have used frogs and chicks that were induced to vomit by emetic agents to test anti-nausea and/or anti-emetic agents for years (Khan, R. A., et al., 2005 "Preliminary Screening of Methanol and Butanol Extracts of *Tamarindus indica* for Anti-Emetic Activity," J. Basic and Applied Sciences, Vol. 1, No. 2; Kawai, T., et al., 1994 "Anti-emetic principles of *Magnolia obovata* and *Zingiber officinale*." Planta Med. 60: 17-20; Kinoshita, K., et al., 1996. "Anti-emetic principles of *Inula linariaefolia* flowers and Forsythia suspense fruits", Phytomedicine 3: 51-58; Tai, T., et al., 1995. "Anti-emetic principles of *Poria cocos*." Plants Med. 61: 493-590; Akita, Y., et al., 1998. "New assay method for surveying anti-emetic compounds from natural sources." Nat Prod Sci 4(2): 72-77; Yang, Y., et al., 1999. "Anti-emetic principles of *Pogostemon cabin* (blanco) benth." Phytomedicine 6(2):89-93; all of which are incorporated herein by reference in their entireties and particularly for their teachings relating to assays and screening methods for detecting/characterizing anti-nausea/anti-emetic agents). Given the presently disclosed novel anti-nausea/anti-emetic activity of the *Houttuynia cordata* extracts, coupled with the knowledge and skill in the art with respect to standard fractionation and purification methods, particular aspects of the invention provide not only for the heat-distilled *Houttuynia cordata* extract (e.g., of Example 10), but for routine fractionation, concentration, and/or purification of the anti-nausea/anti-emetic activity to provide for fractionated, concentrated, and/or purified derivative fractions of the heat-distilled *Houttuynia cordata* extract (e.g., of Example 10).

The invention claimed is:

1. A method for preparing heat-treated, fractionated thymus extract composition, comprising:
    homogenizing thymus tissue with aqueous hypotonic homogenization fluid to produce an aqueous thymus homogenate;
    removing tissue debris from the aqueous thymus homogenate to produce a primary supernatant;
    heat denaturing the primary supernatant, and clarifying the denatured primary supernatant by use of at least one of low-speed centrifugation and filtration, to produce a clarified supernatant;
    separating molecules having molecular weights less than 3.5 kDa from the clarified supernatant; and
    separating molecules having molecular weight greater than about 30 kDa from the heat-treated, fractionated thymus extract composition, wherein a heated, fractionated thymus extract composition comprising proteins or polypeptides having molecular weights in the range of 3.5 kDa to 30 kDa is provided.

2. The method of claim 1, further comprising further clarifying of the clarified supernatant by high-speed centrifugation to produce a final clarified supernatant fraction.

3. The method of claim 2, further comprising sterilizing the final clarified supernatant fraction to produce a sterile final clarified supernatant fraction.

4. The method of claim 3, wherein sterilizing is achieved by passing the final clarified supernatant fraction through a membrane filter.

5. The method of claim 1, wherein the initial ratio of thymus tissue to aqueous homogenization fluid is about 350 g wet weight of thymus tissue to about 0.7 L of homogenization fluid.

6. The method of claim 1, wherein removing tissue debris from the aqueous thymus homogenate is achieved by a combination of low-speed centrifugation and crude filtration.

7. The method of claim 1, wherein heat denaturing and clarifying of the primary supernatant is achieved by heat denaturation, followed by low-speed centrifugation and crude filtration to remove particulate matter.

8. The method of claim 2, further comprising lyophilization of the final clarified supernatant fraction.

9. The method of claim 1, wherein no steps involving exogenously added protease digestion, or extraction with organic solvents are used.

10. A method for preparing a thymus extract composition, comprising:
homogenizing thymus tissue with aqueous hypotonic homogenization fluid to produce an aqueous thymus homogenate;
removing tissue debris from the aqueous thymus homogenate to produce a primary supernatant;
heat denaturing the primary supernatant, and clarifying the denatured primary supernatant by use of at least one of low-speed centrifugation and filtration to produce an intermediate clarified supernatant;
concentrating the intermediate clarified supernatant to produce a concentrated intermediate fraction;
separating molecules having molecular weights less than 3.5 kDa from the concentrated intermediate fraction; and
separate molecules having molecular weights greater than 30 kDa from the heat-treated, fractionated thymus extract composition, wherein a heat-treated, fractionated thymus extract composition comprising proteins or polypeptides having molecular weights in the range of 3.5 kDa to 30 kDa is provided.

11. The method of claim 10, comprising further clarifying of the concentrated intermediate fraction by high-speed centrifugation to produce a final clarified supernatant fraction.

12. The method of claim 11, further comprising adjusting at least one of the pH or ionic strength of the fraction having proteins or polypeptides of molecular weight of 3.5 kDa to 30 kDa to a physiological or therapeutically compatible value, to produce a pH-adjusted fraction or ionic strength-adjusted fraction.

13. The method of claim 12, wherein adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v.

14. The method of claim 12, further comprising sterilizing the pH-, or ionic strength-adjusted fraction to produce a sterile pH-adjusted fraction, or ionic strength-adjusted fraction.

15. The method of claim 14, wherein sterilizing is achieved by passing the fraction through a membrane filter.

16. The method of claim 10, wherein the initial ratio of thymus tissue to aqueous homogenization fluid is about 350 g wet weight of thymus tissue to about 0.7 L of homogenization fluid.

17. The method of claim 10, wherein removing tissue debris from the aqueous thymus homogenate is achieved by a combination of low-speed centrifugation and crude filtration.

18. The method of claim 10, wherein heat denaturing and clarifying of the primary supernatant is achieved by heat denaturation, followed by low-speed centrifugation and crude filtration to remove particulate matter.

19. The method of claim 10, wherein concentrating the intermediate supernatant involves concentrating and fractionating, and wherein the concentrating and fractionating is achieved by adding ammonium sulfate to the intermediate clarified supernatant, followed by low-speed centrifugation and suspension of the resulting ammonium sulfate pellet in an aqueous solution to provide a concentrated intermediate fraction.

20. The method of claim 19, wherein separating molecules having molecular weights less than 3.5 kDa from the concentrated intermediate fraction comprises dialysis of the concentrated intermediate fraction, followed by high-speed centrifugation to remove particulate matter, to provide for a clarified concentrated intermediate fraction lacking proteins or polypeptides having molecular weights less than 3.5 kDa.

21. The method of claim 20, wherein separating molecules having molecular weights greater than 30 kDa from the heat-treated, fractionated thymus extract composition, is achieved by passing the clarified concentrated intermediate fraction lacking proteins or polypeptides having molecular weights less than 3.5 kDa consecutively through a first and a second membrane filter having exclusion limits of about 100 kDa and about 30 kDa, respectively, and collecting the filtrate.

22. The method of claim 11, further comprising lyophilization of the heat-treated, fractionated thymus extract composition comprising proteins or polypeptides having molecular weights in the range of 3.5 kDa to 30 kDa.

* * * * *